United States Patent
Park et al.

(10) Patent No.: US 9,765,383 B2
(45) Date of Patent: *Sep. 19, 2017

(54) APPARATUS AND METHOD FOR AUTOMATICALLY ANALYZING BIOLOGICAL SAMPLES

(71) Applicant: BIONEER CORPORATION, Daejeon (KR)

(72) Inventors: Han Oh Park, Daejeon (KR); Yang Won Lee, Daejeon (KR); Jong-Kab Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 36 days.

This patent is subject to a terminal disclaimer.

(21) Appl. No.: 14/377,537

(22) PCT Filed: Feb. 7, 2013

(86) PCT No.: PCT/KR2013/000985
§ 371 (c)(1),
(2) Date: Aug. 8, 2014

(87) PCT Pub. No.: WO2013/119049
PCT Pub. Date: Aug. 15, 2013

(65) Prior Publication Data
US 2015/0037803 A1    Feb. 5, 2015

(30) Foreign Application Priority Data
Feb. 10, 2012 (KR) .......... 10-2012-0013757

(51) Int. Cl.
C12M 1/00    (2006.01)
C12Q 1/68    (2006.01)
(Continued)

(52) U.S. Cl.
CPC ....... *C12Q 1/6804* (2013.01); *G01N 35/0099* (2013.01); *B01L 7/52* (2013.01); *G01N 35/1065* (2013.01)

(58) Field of Classification Search
None
See application file for complete search history.

(56) References Cited

U.S. PATENT DOCUMENTS

| 5,443,791 | A | 8/1995 | Cathcart et al. |
| 5,647,994 | A | 7/1997 | Tuunanen et al. |
| (Continued) | | | |

FOREIGN PATENT DOCUMENTS

| EP | 2407557 A2 | 1/2012 |
| JP | 2004317363 A | 11/2004 |
| (Continued) | | |

OTHER PUBLICATIONS

Christof M. Niemeyer et al., "Protocol: Detecting antigens by quantitative immuno-PCR", Nature Protocols, vol. 2, No. 8, (2007),(13 pages total) XP-002450432 doi:10.1038/nprot.2007.267.

(Continued)

*Primary Examiner* — Betty Forman
(74) *Attorney, Agent, or Firm* — Sughrue Mion, PLLC

(57) ABSTRACT

Provided are an apparatus and a method for automatically analyzing biological samples capable of performing the entire processes of dissolving the biological samples in protease and cell lysate to dissolve a nucleic acid in a solution, attaching the nucleic acid to magnetic particles, finally washing the magnetic particle to which the nucleic acid is attached with an organic solvent, drying the magnetic particles using a vacuum pump, eluting the target nucleic acid attached to the magnetic particles in an aqueous solution, adding and mixing the eluted target nucleic acid into a vessel containing a nucleic acid amplification reagent, real- (Continued)

time detecting amplification by irradiating excitation light to a reactor simultaneously with regulating a temperature to perform amplification to measure fluorescence, inactivating an amplified product using an ultraviolet lamp after amplification, obtaining an image through electrophoresis, and analyzing a molecular weight in a single apparatus.

30 Claims, 26 Drawing Sheets

(51) Int. Cl.
*G01N 35/00* (2006.01)
*B01L 7/00* (2006.01)
*G01N 35/10* (2006.01)

(56) References Cited

U.S. PATENT DOCUMENTS

| | | | |
|---|---|---|---|
| 5,702,950 | A | 12/1997 | Tajima |
| 6,187,270 | B1 | 2/2001 | Schmitt et al. |
| 2002/0014443 | A1* | 2/2002 | Hansen ............... B01L 7/52 209/213 |
| 2002/0028923 | A1* | 3/2002 | Cowsert ............... C40B 50/02 536/23.1 |
| 2003/0224395 | A1 | 12/2003 | Jovanovich et al. |
| 2007/0117092 | A1 | 5/2007 | Sadarangani et al. |
| 2008/0038813 | A1* | 2/2008 | Chen .................... A61B 5/1427 435/287.2 |
| 2011/0009608 | A1* | 1/2011 | Kim .................... C12N 15/1013 536/25.41 |

FOREIGN PATENT DOCUMENTS

| | | |
|---|---|---|
| JP | 2011516075 A | 5/2011 |
| KR | 10-0673811 B1 | 1/2007 |
| KR | 10-2010-0102560 A | 9/2010 |
| KR | 10-2011-0121588 A | 11/2011 |
| WO | 2004/089545 A1 | 10/2004 |
| WO | 2006/121295 A1 | 11/2006 |
| WO | 2011136624 A3 | 11/2011 |

OTHER PUBLICATIONS

Canadian Intellectual Property Office, Communication dated Oct. 26, 2015, issued in counterpart application No. 2,864,260.
European Patent Office, Communication dated Aug. 13, 2015, issued in counterpart European Application No. 13746518.3.

* cited by examiner

【FIG. 1】
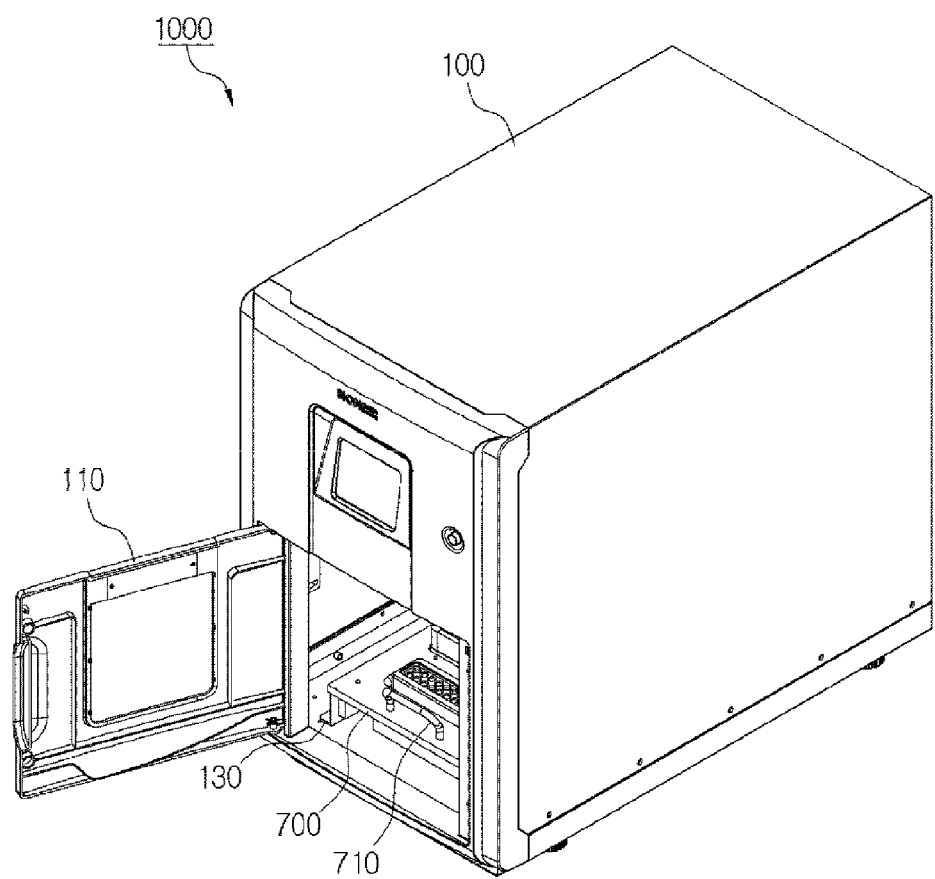

[FIG. 2]
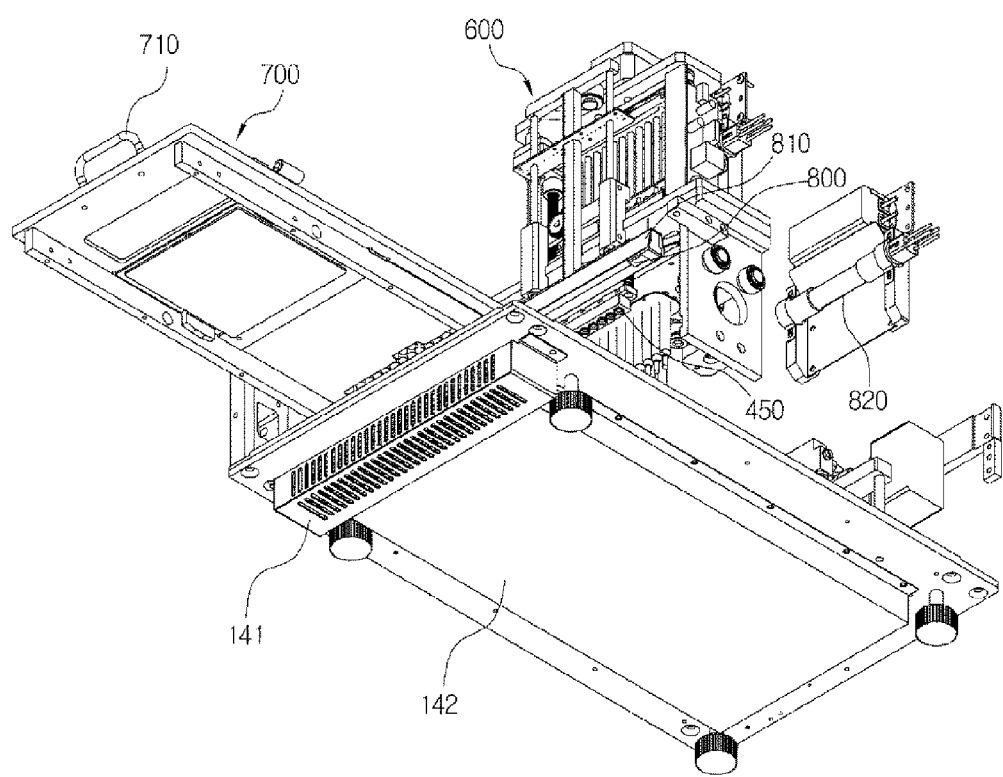

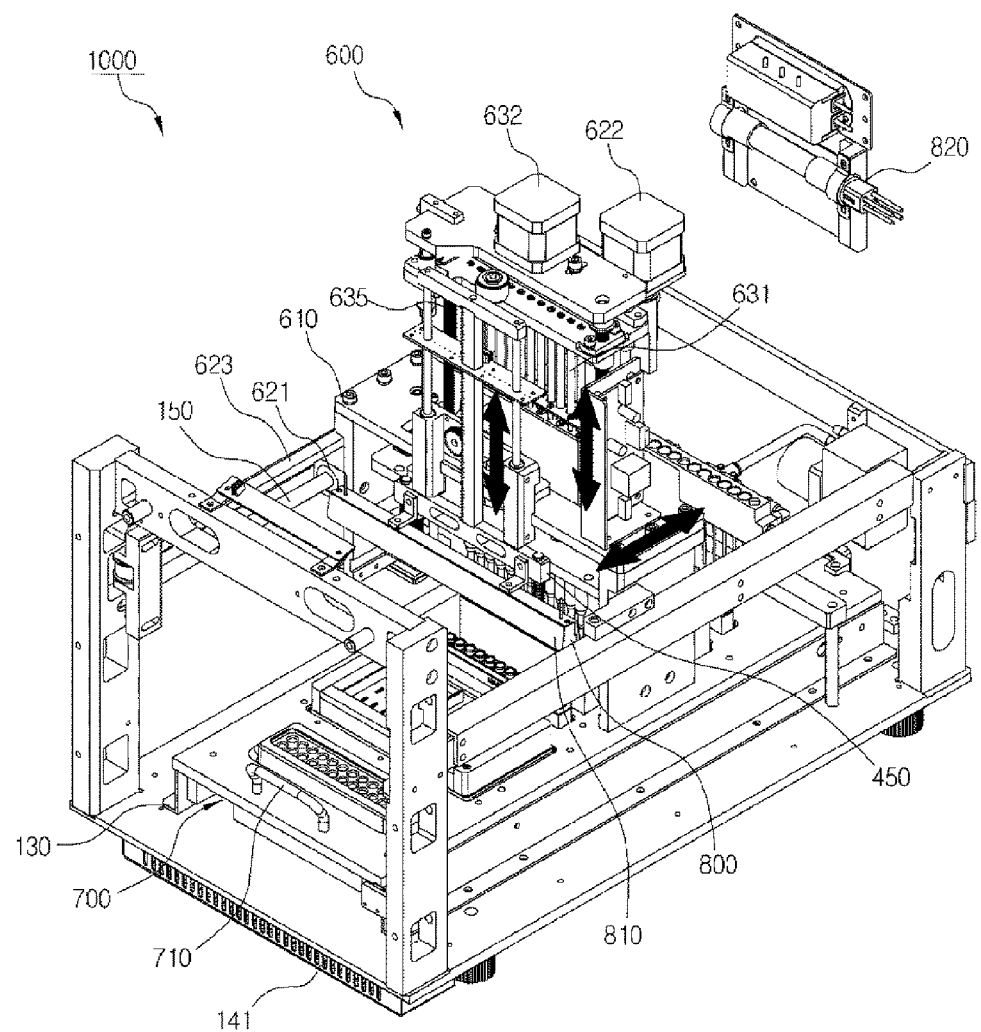
[FIG. 3]

[FIG. 4]
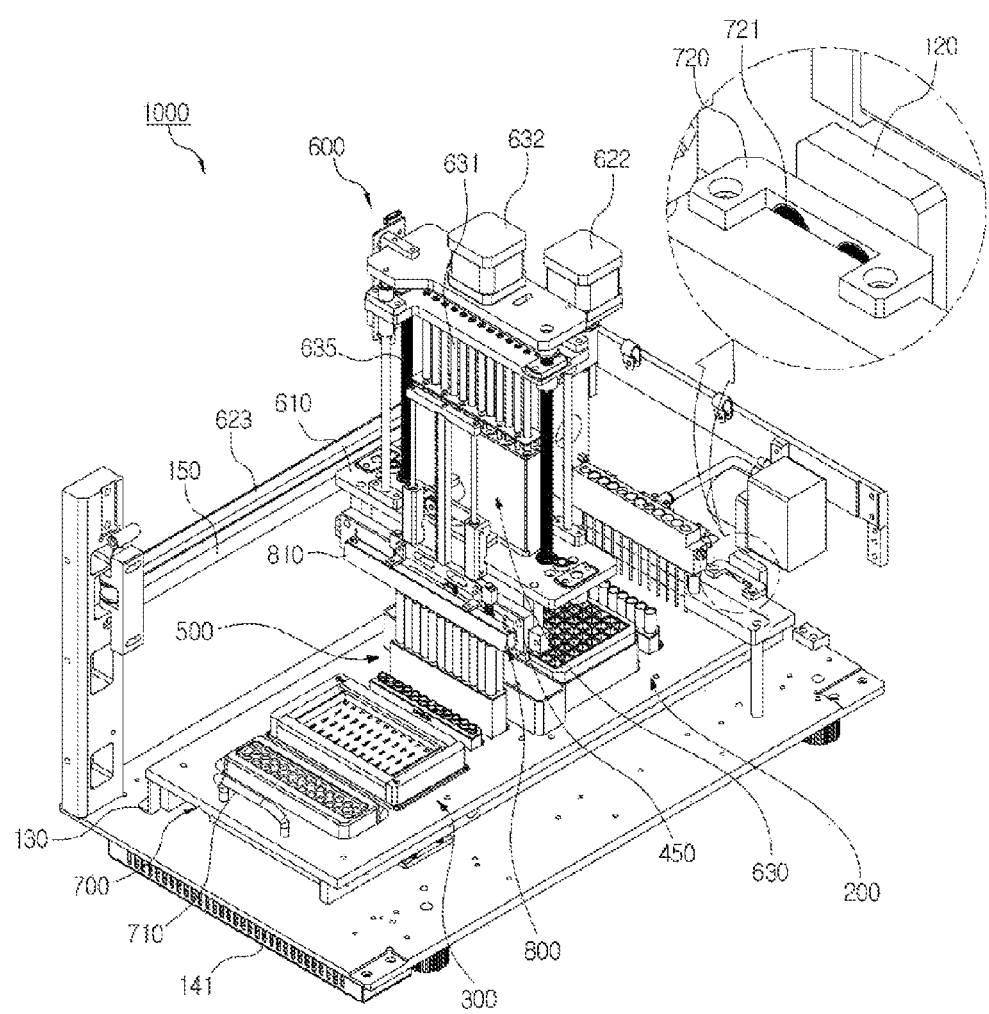

【FIG. 5】
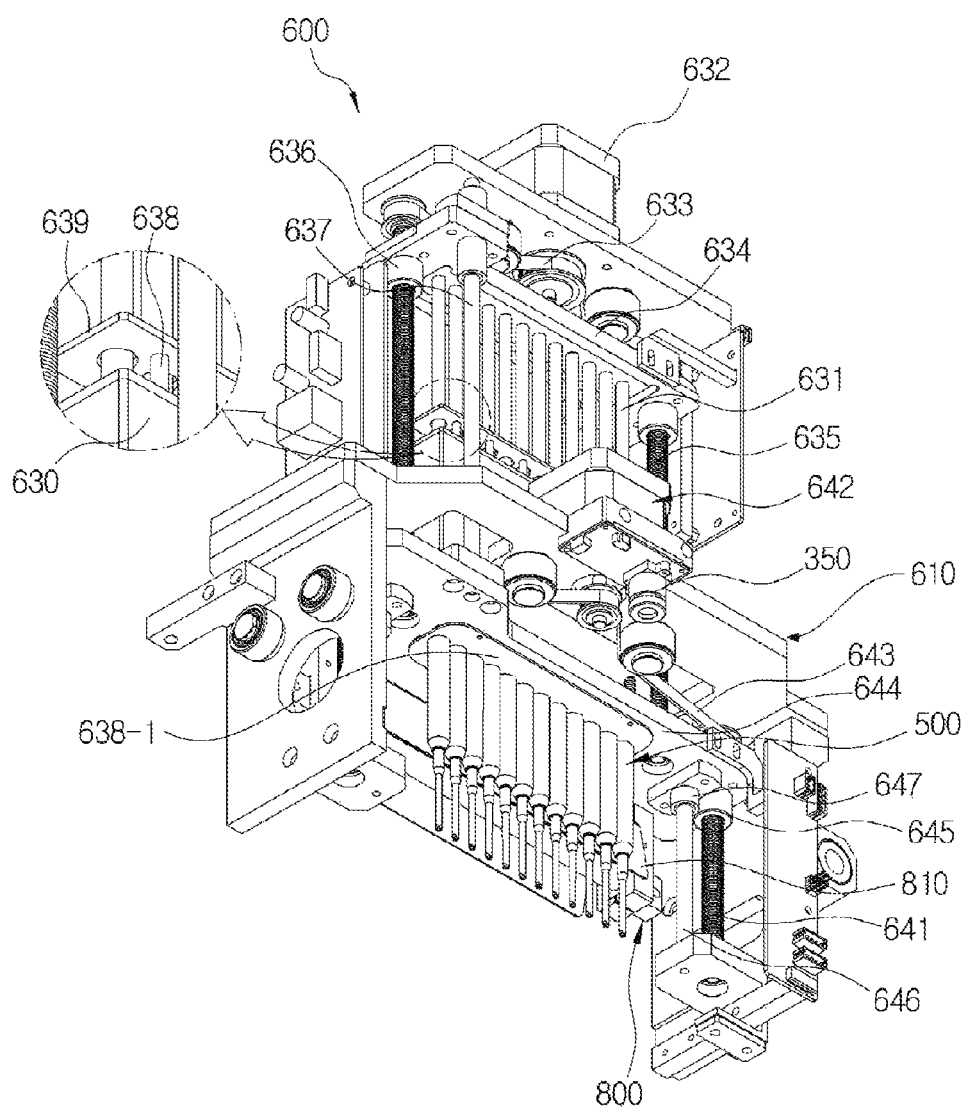

[FIG. 6]
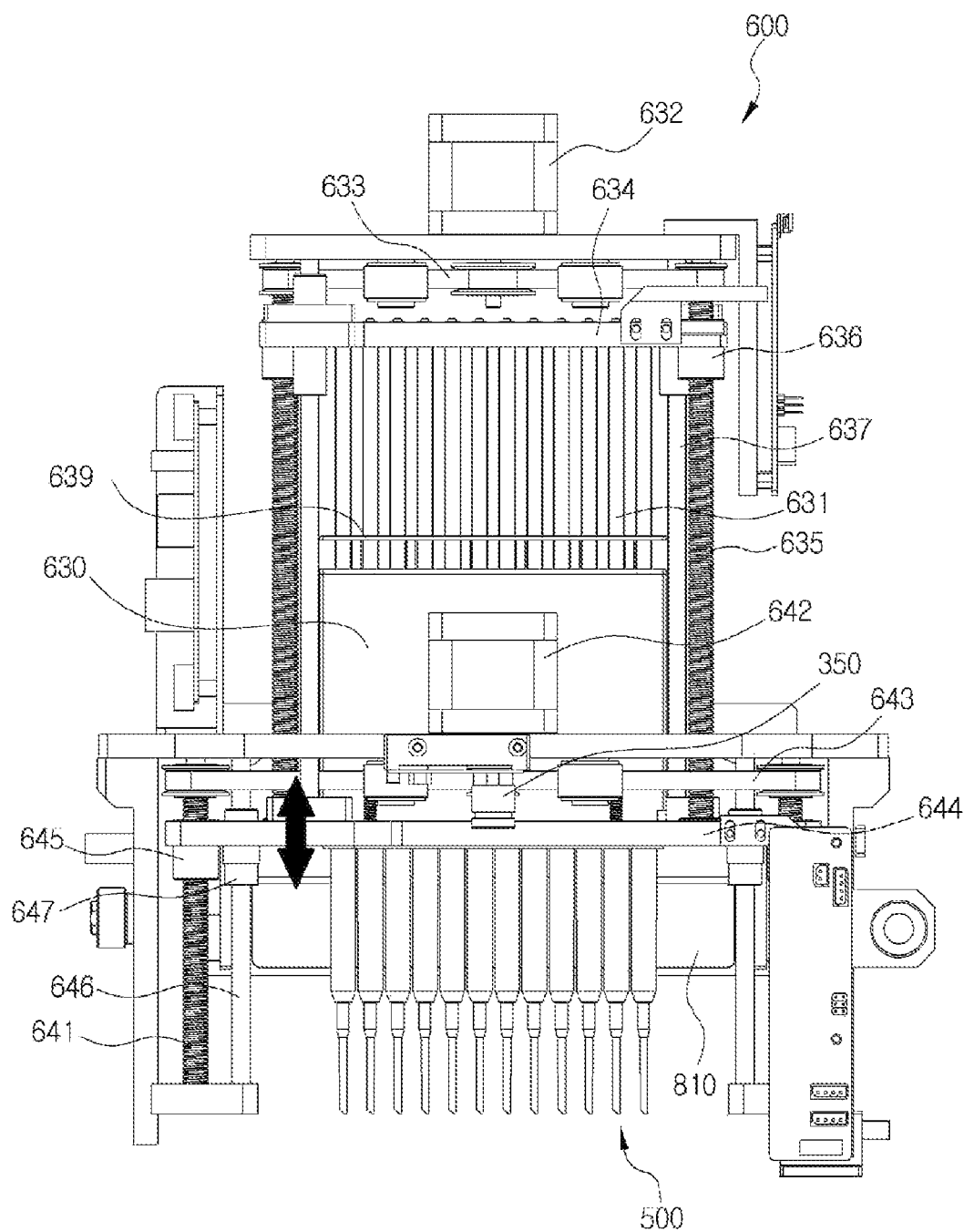

[FIG. 7]
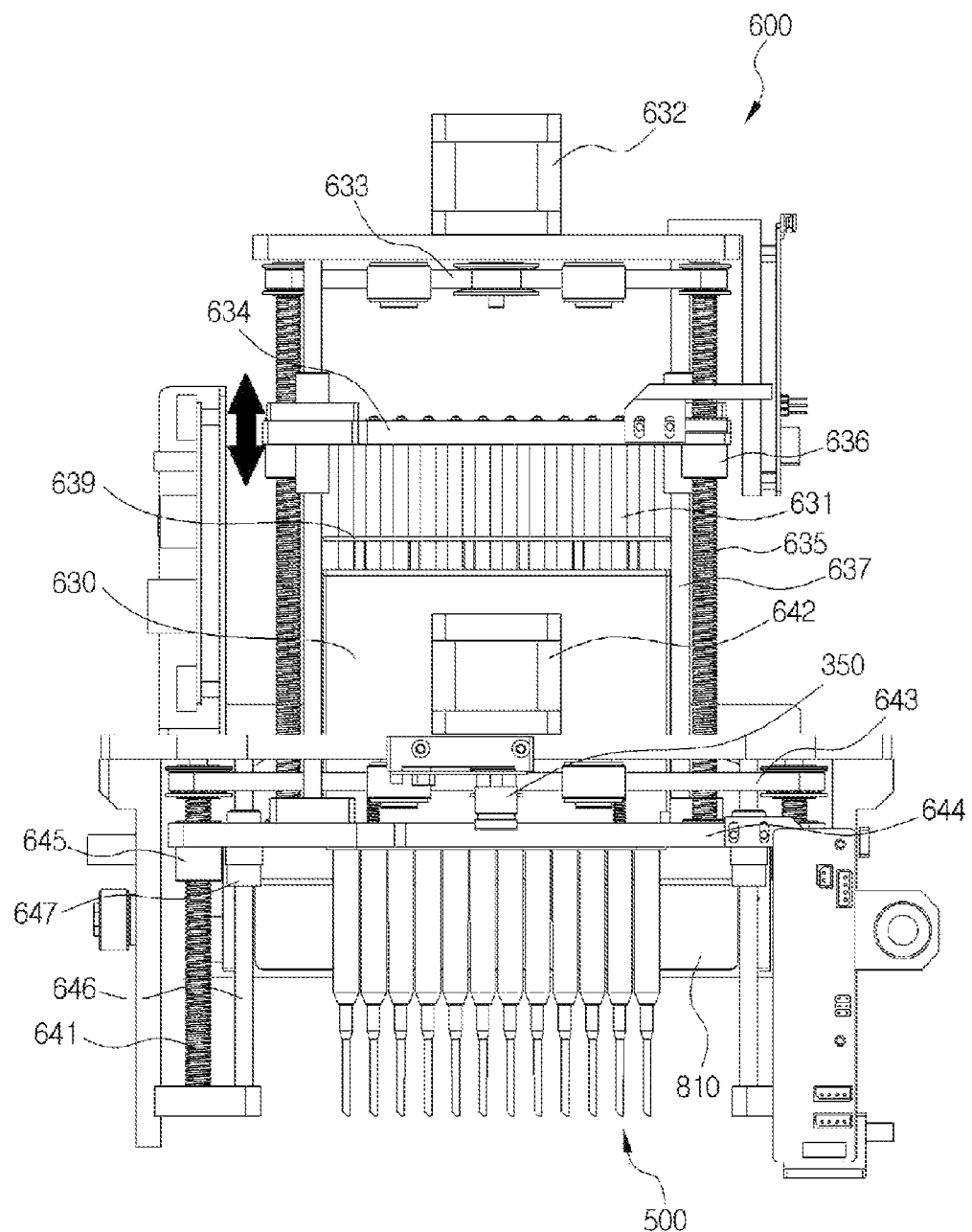

[FIG. 8]
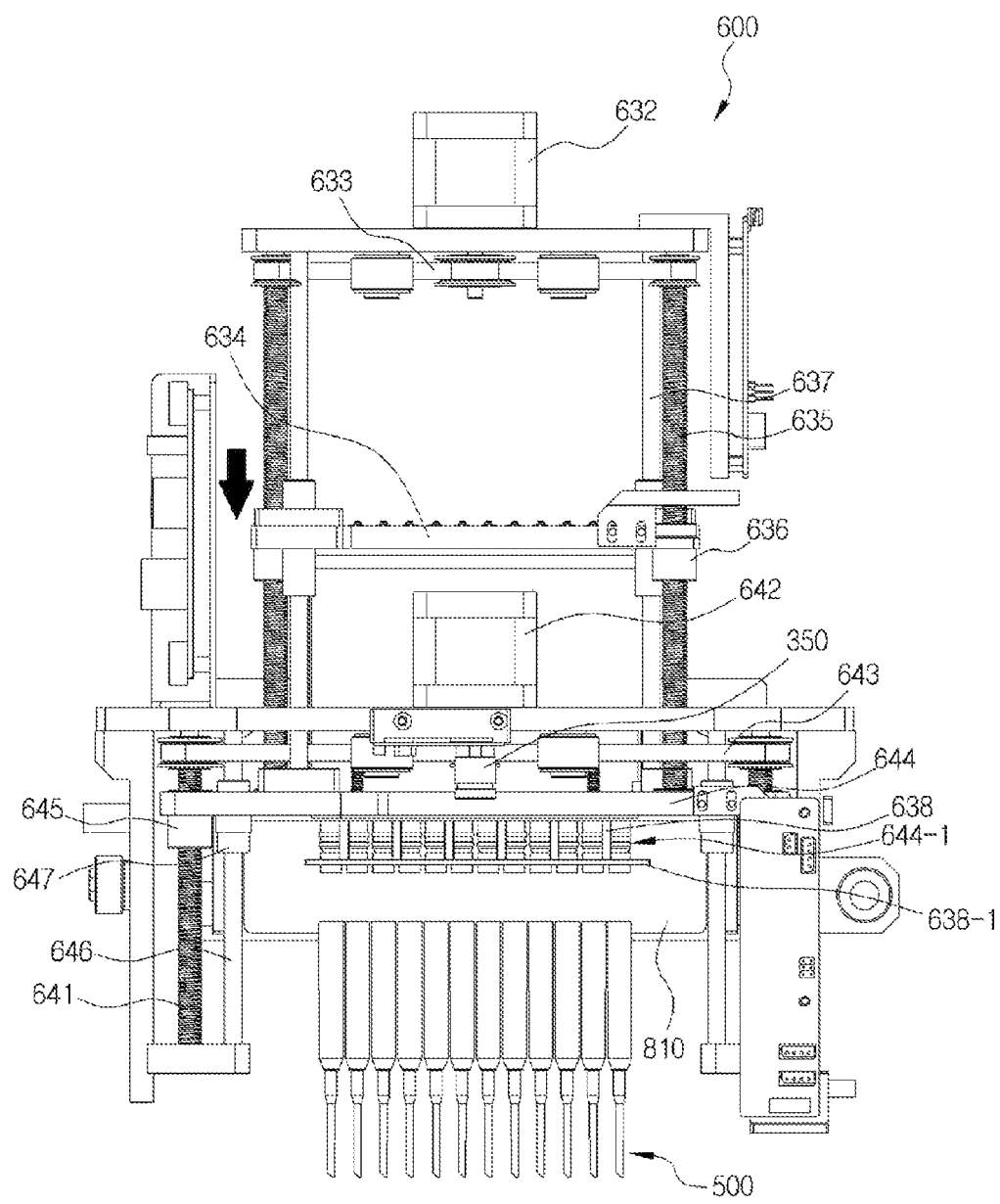

【FIG. 9】
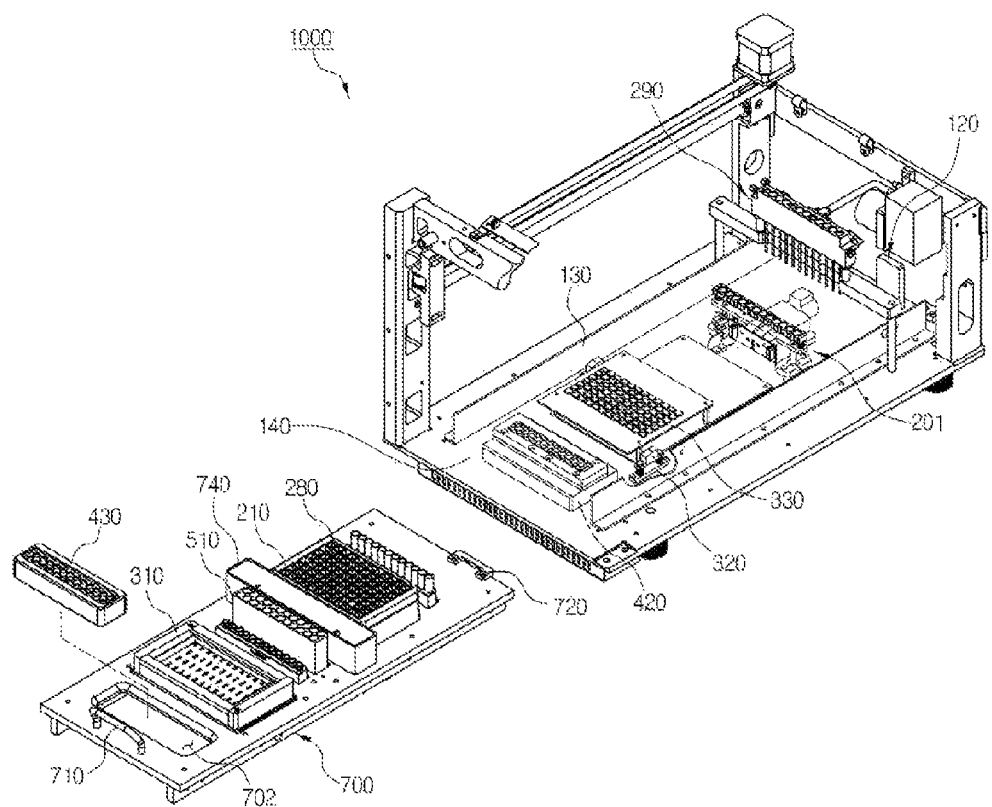

[FIG. 10]
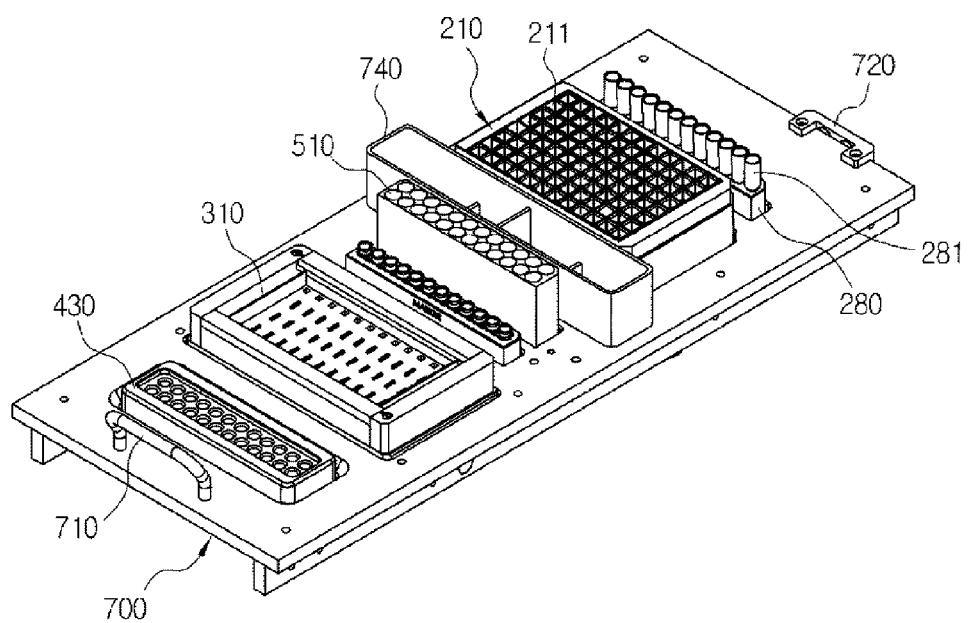

【FIG. 11】
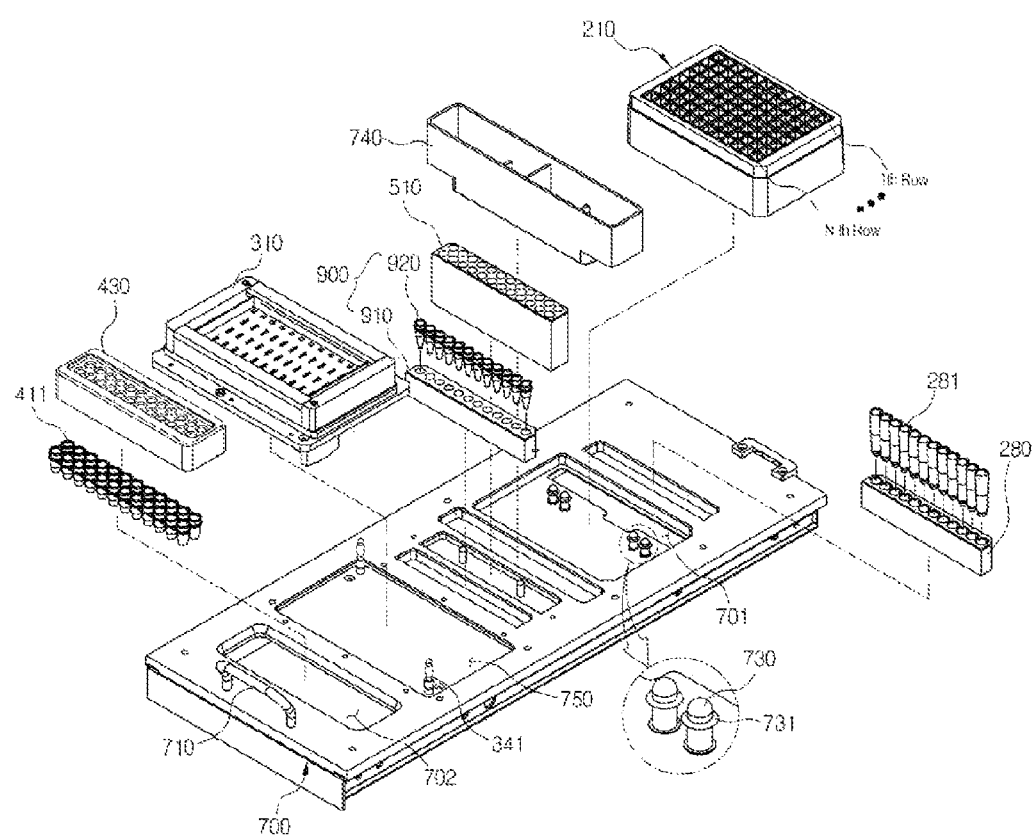

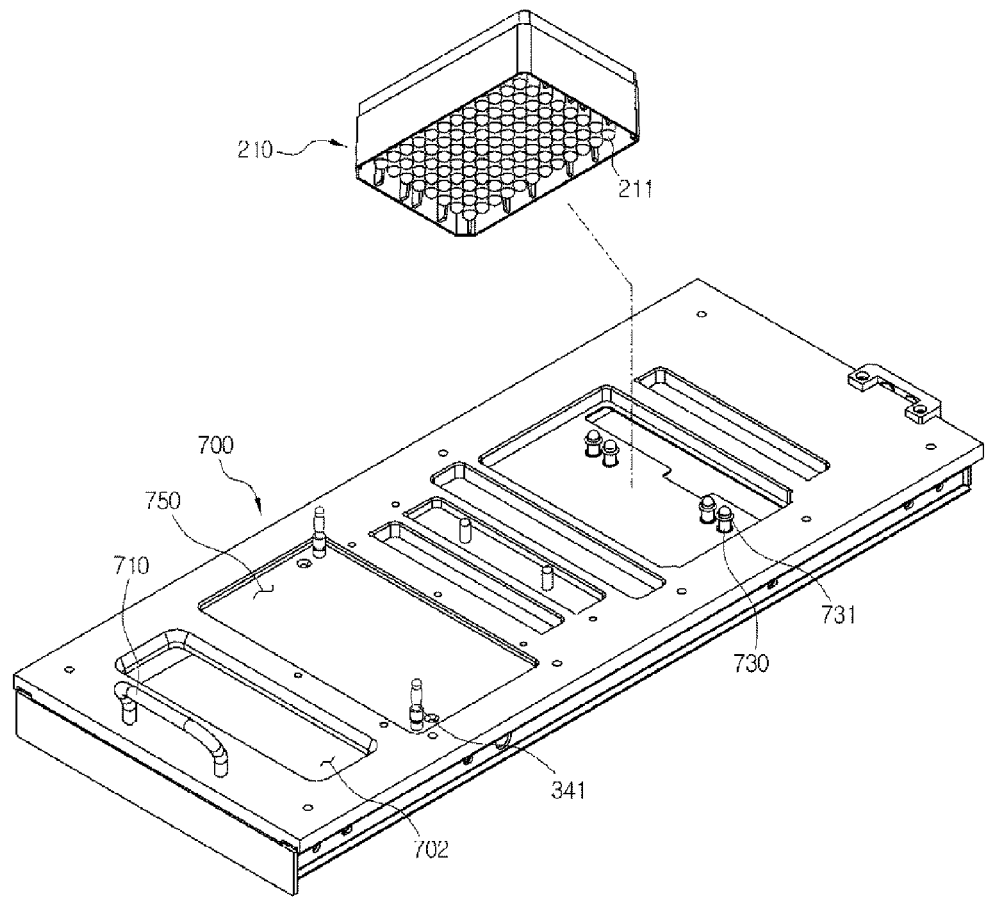
【FIG. 12】

【FIG. 13】
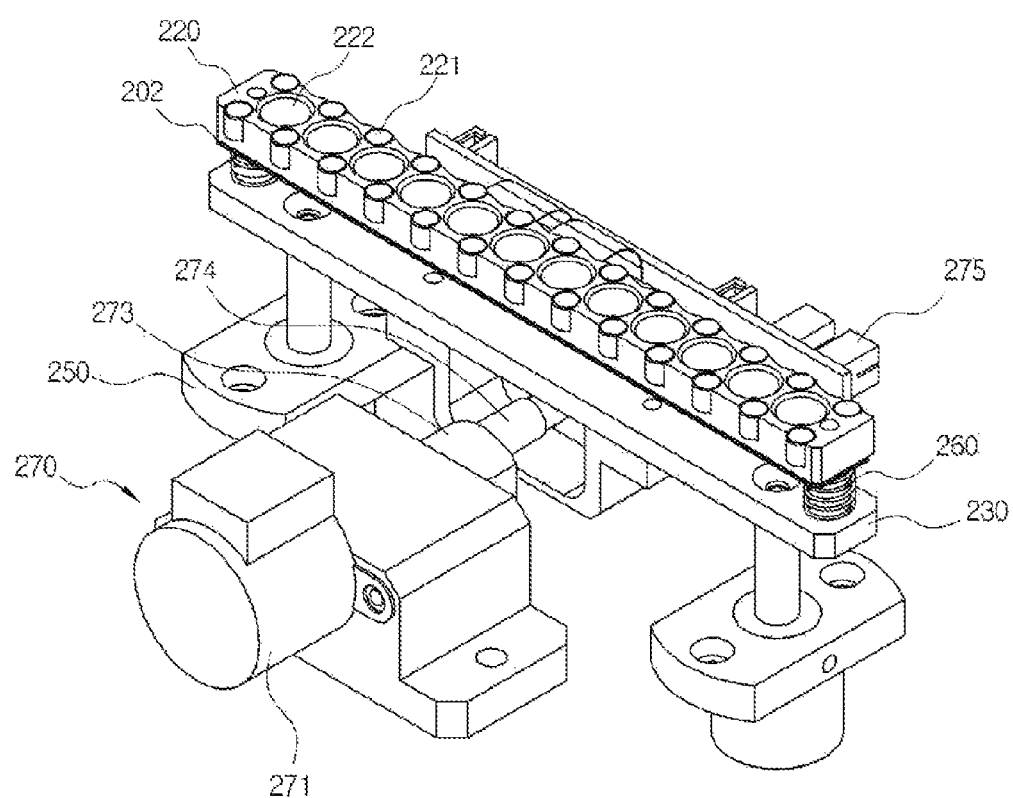

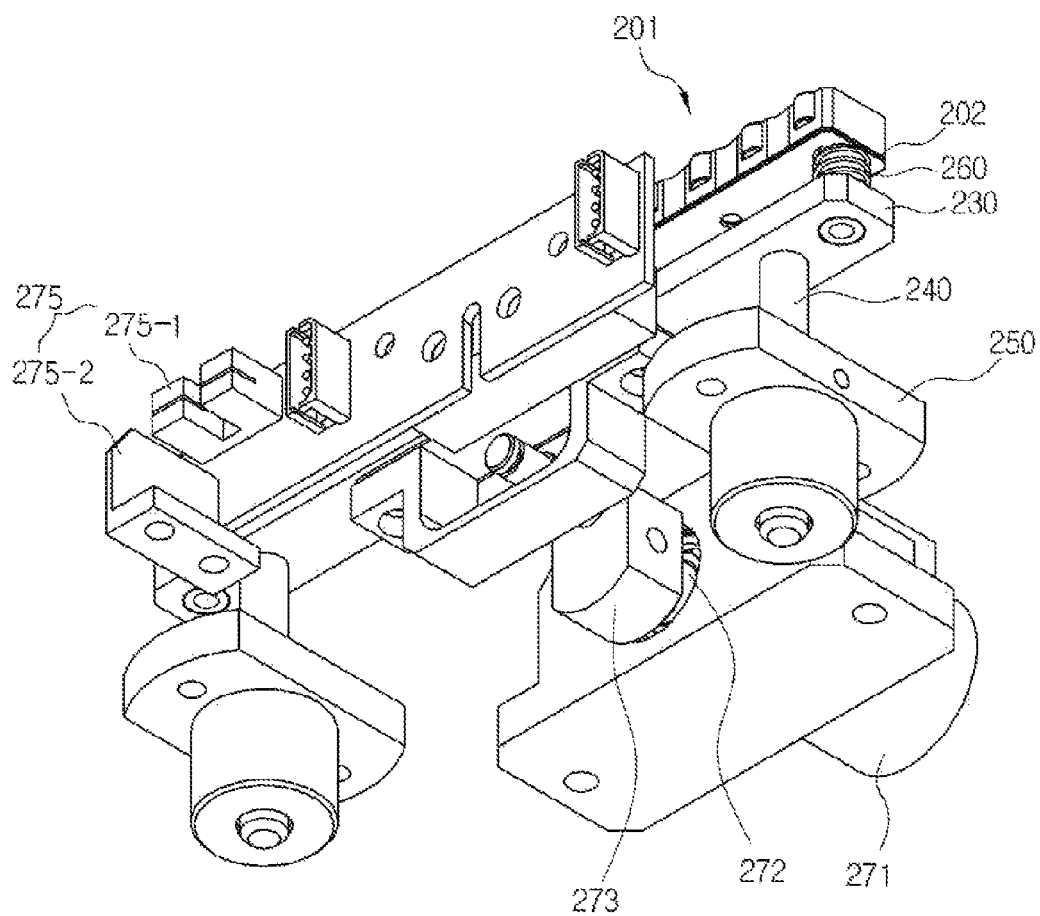
[FIG. 14]

【FIG. 15】
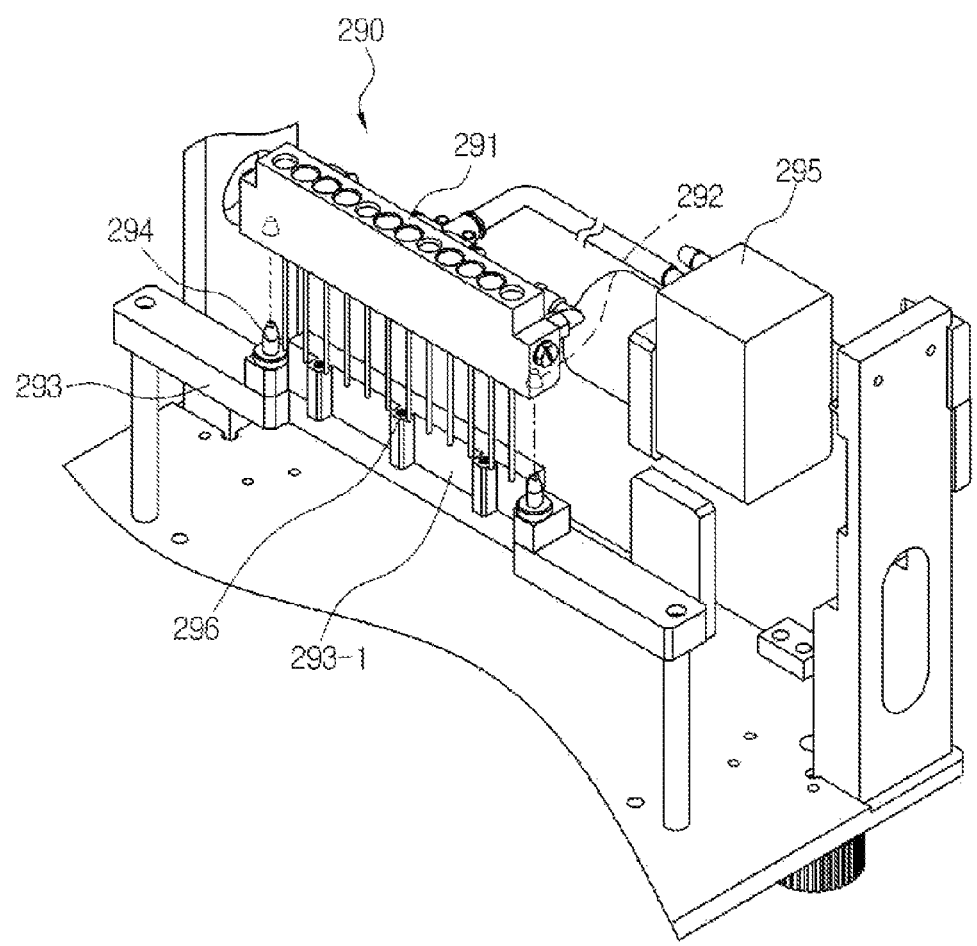

【FIG. 16】
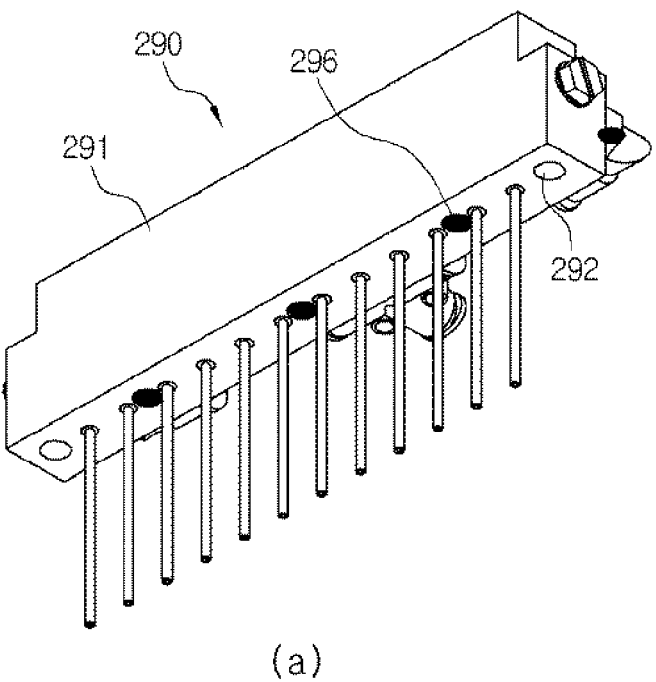
(a)
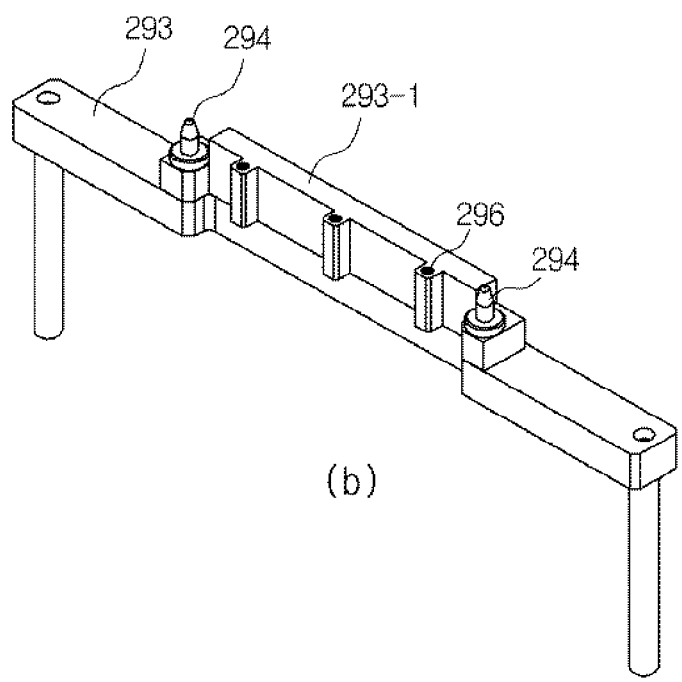
(b)

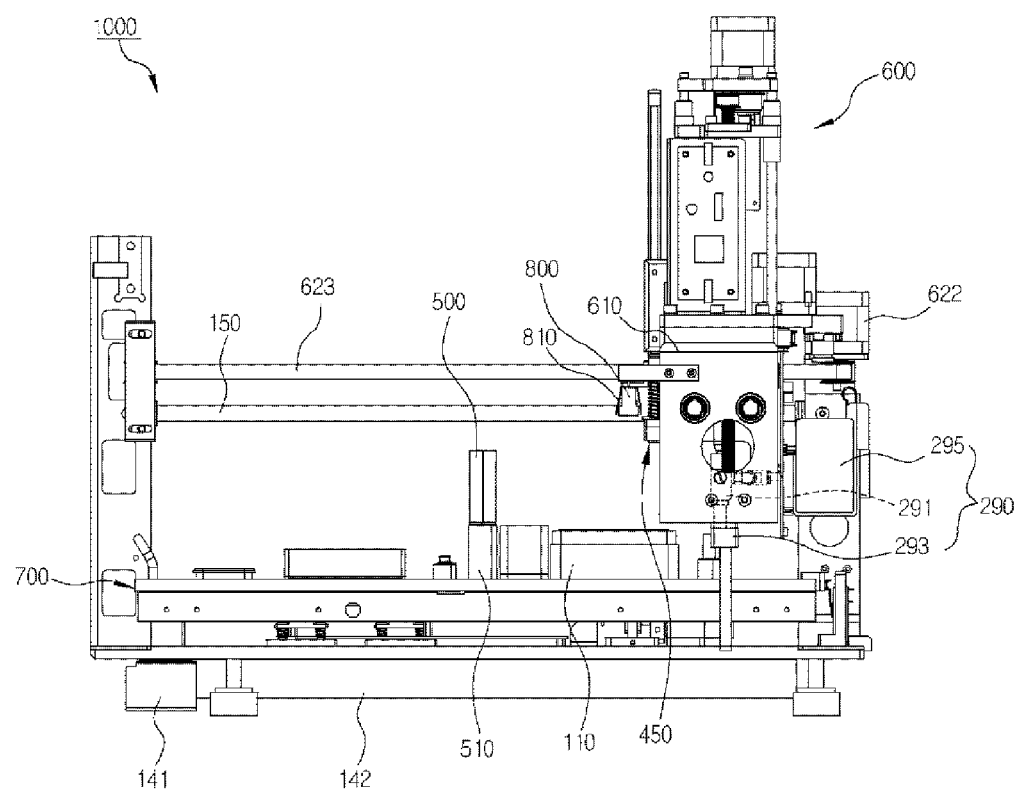
[FIG. 17]

【FIG. 18】
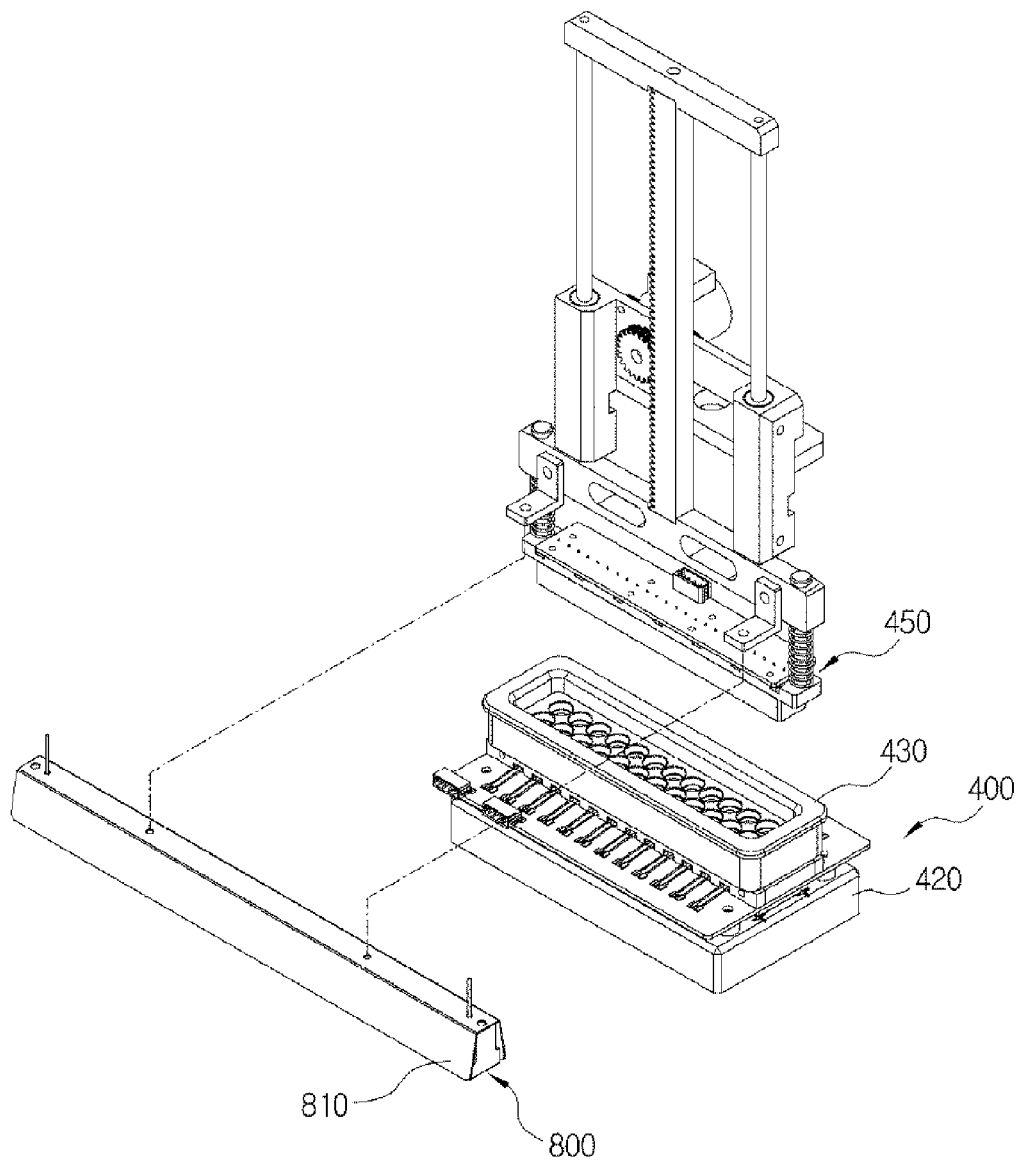

【FIG. 19】
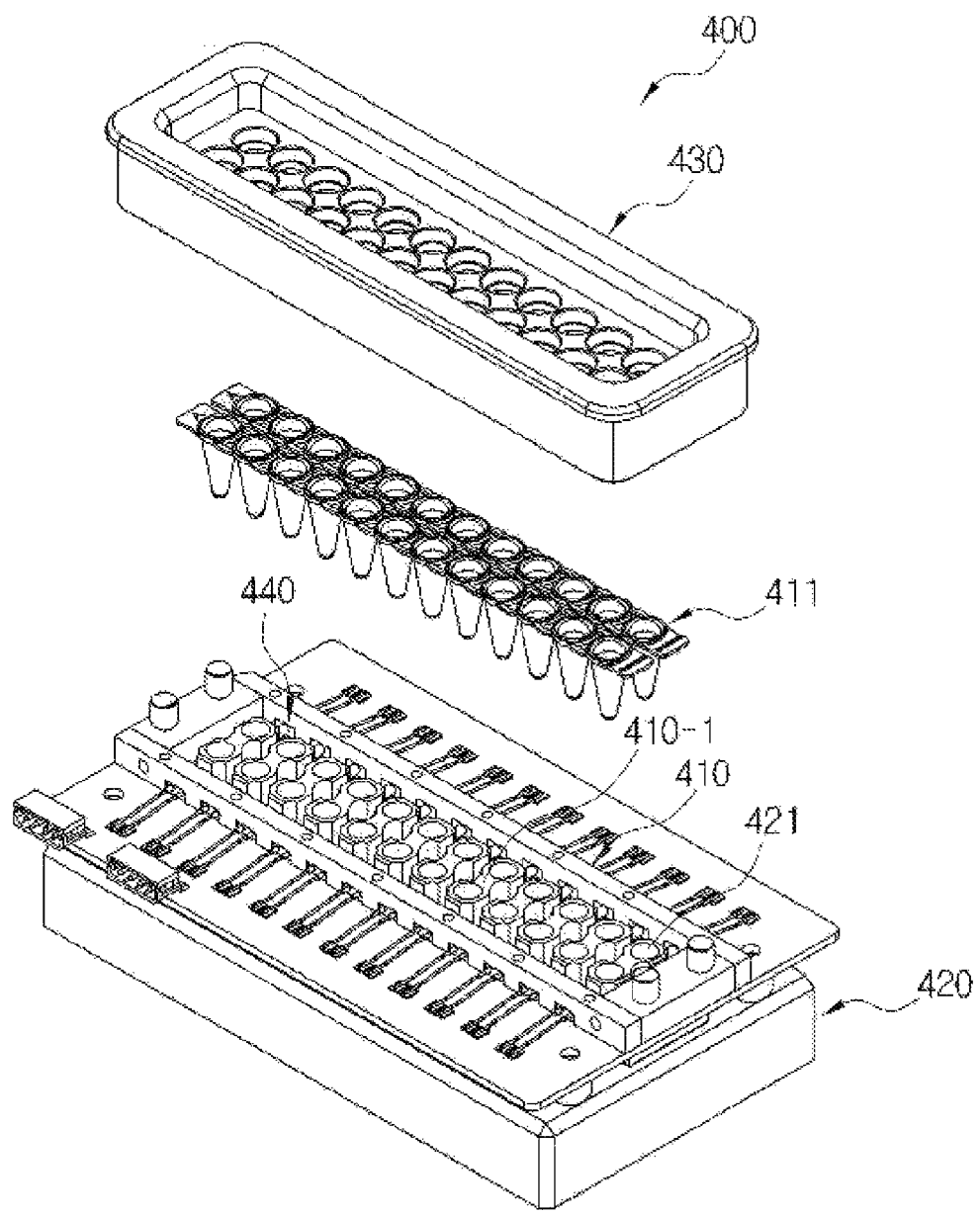

[FIG. 20]
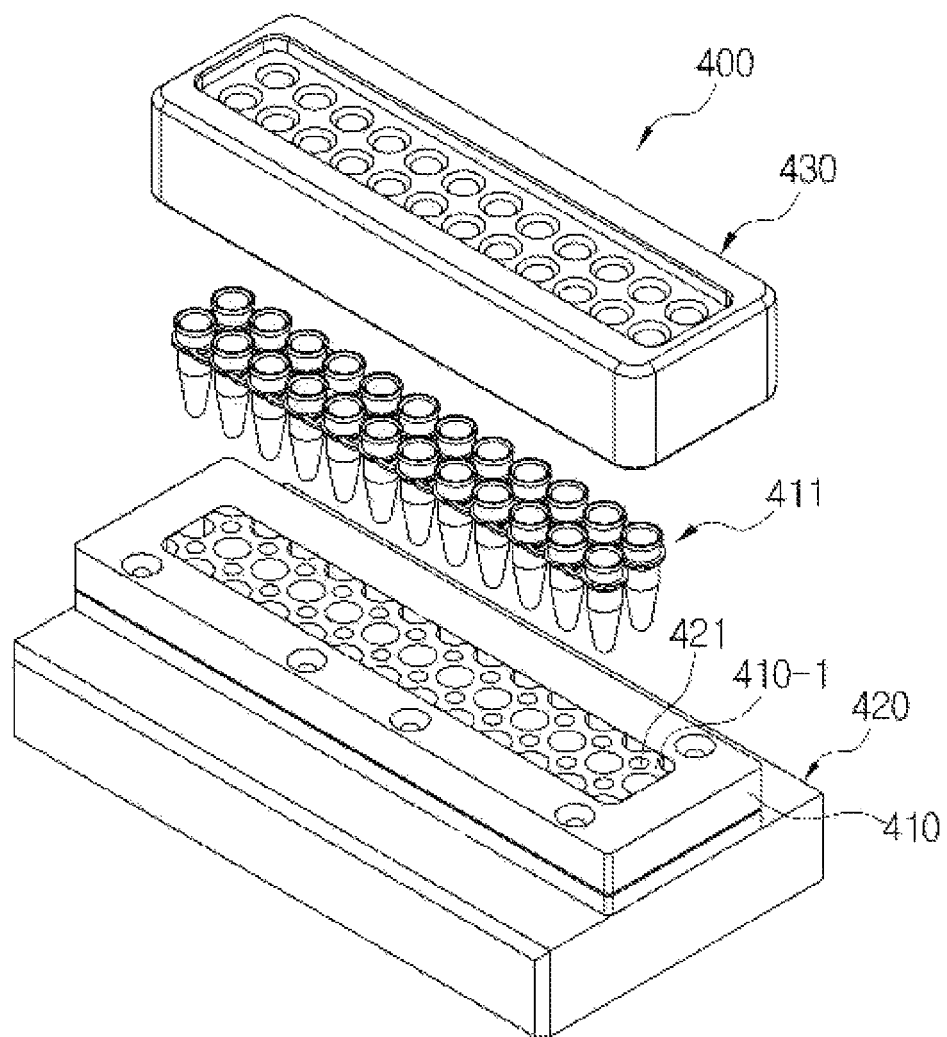

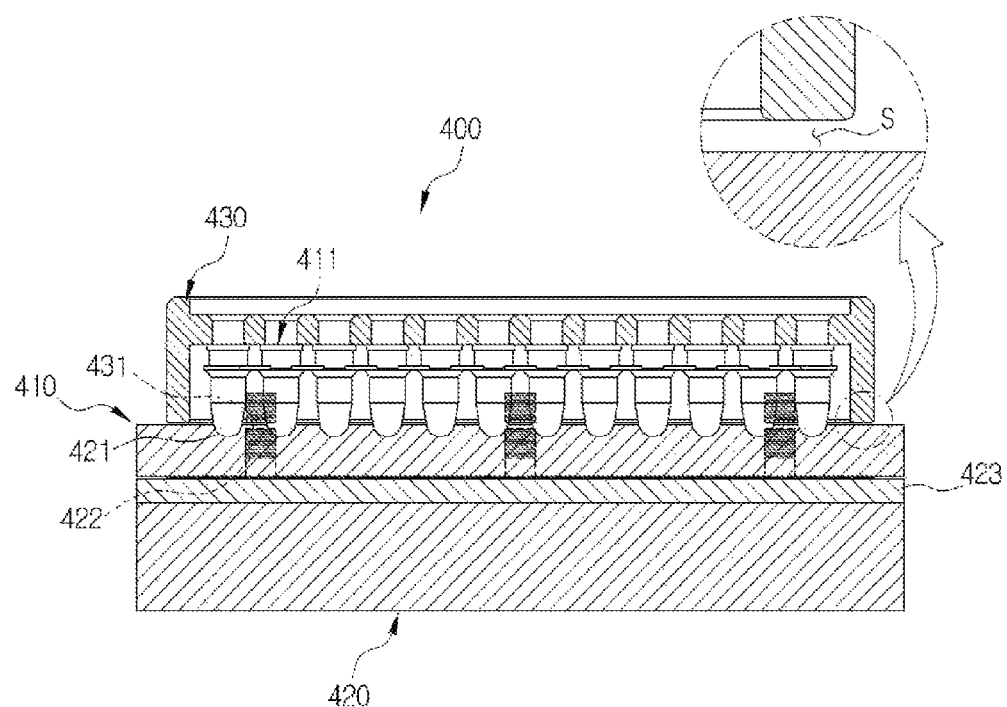
[FIG. 21]

[FIG. 22]
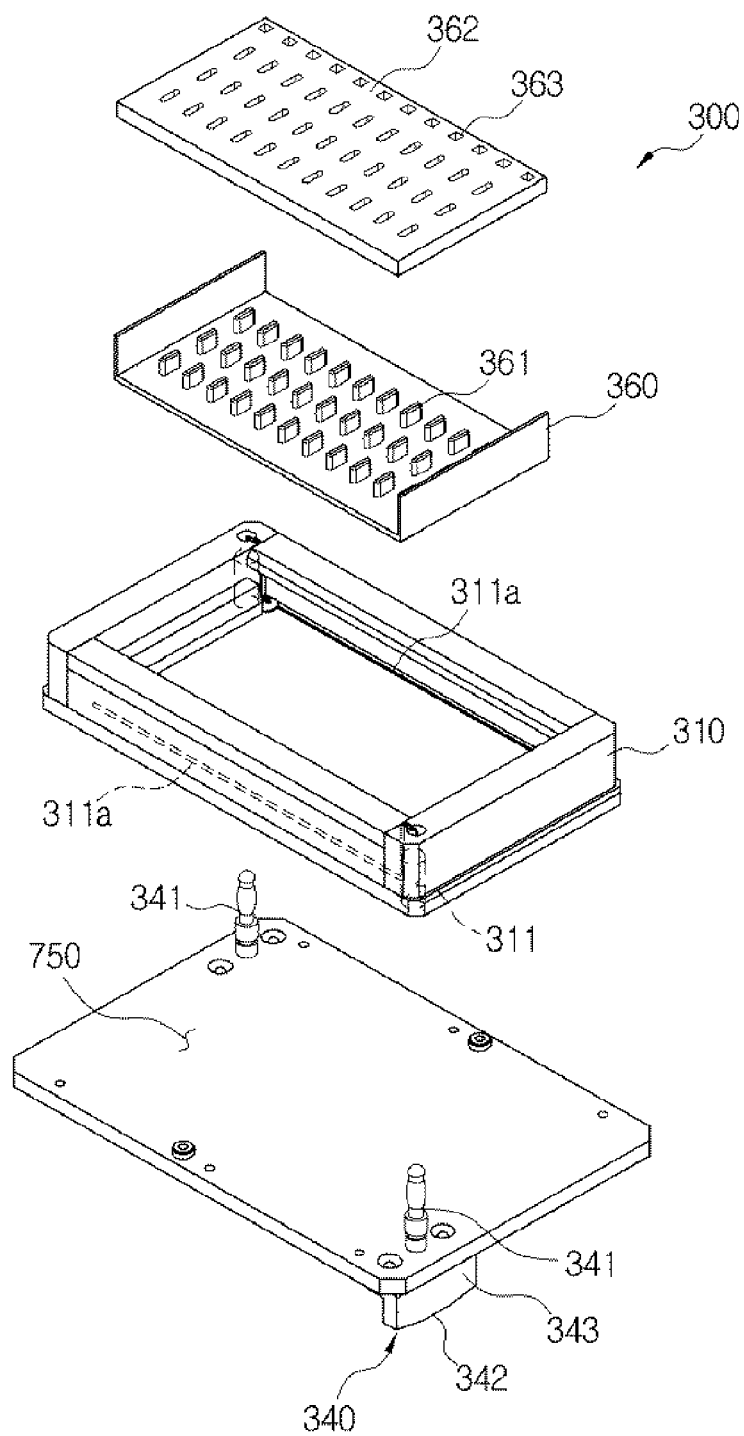

[FIG. 23]
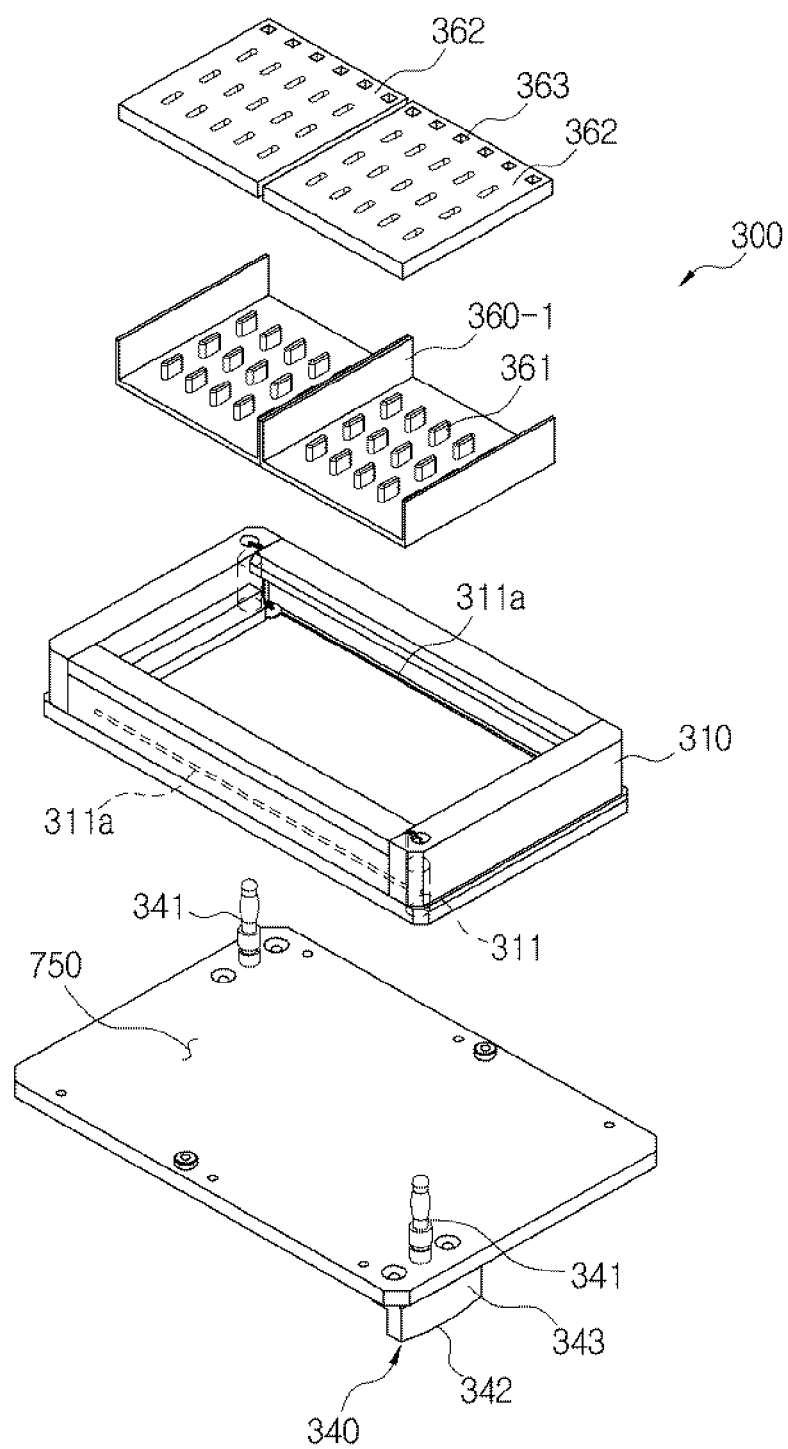

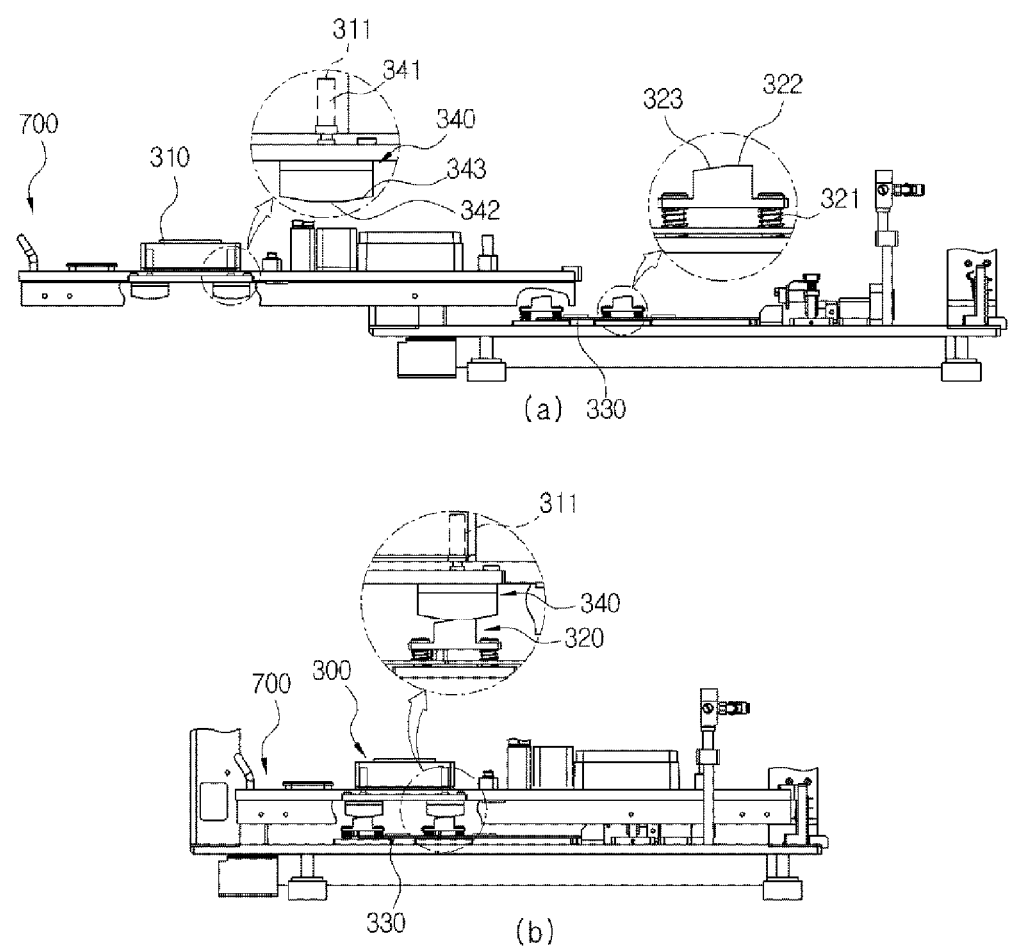
[FIG. 24]

[FIG. 25]
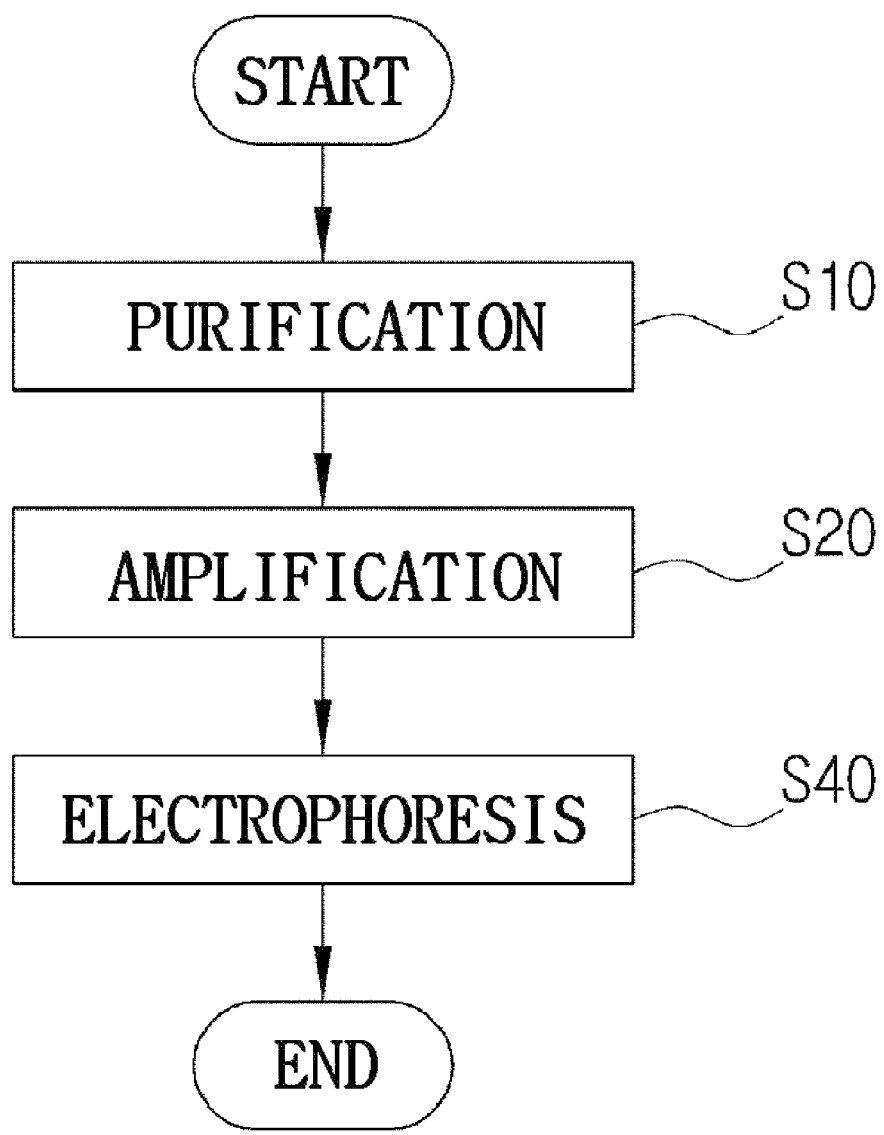

[FIG. 26]
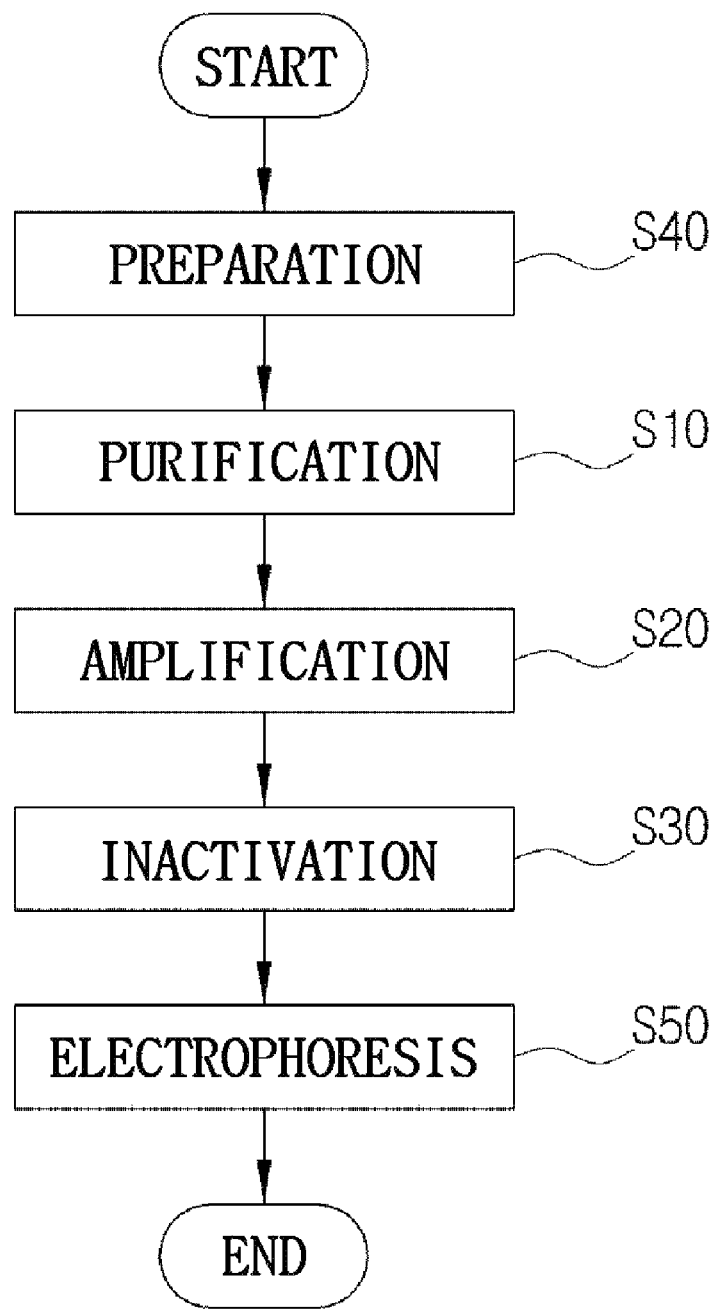

APPARATUS AND METHOD FOR AUTOMATICALLY ANALYZING BIOLOGICAL SAMPLES

CROSS REFERENCE TO RELATED APPLICATIONS

This is a National Stage of International Application No. PCT/KR2013/000985 filed Feb. 7, 2013, claiming priority based on Korean Patent Application No. 10-2012-0013757 filed Feb. 10, 2012, the contents of all of which are incorporated herein by reference in their entirety.

TECHNICAL FIELD

The present invention relates to an apparatus and method for automatically analyzing biological samples, and more particularly, to an apparatus and method for automatically analyzing biological samples capable of performing the entire process of purifying a target nucleic acid from the biological samples, performing polymerase chain reaction (PCR), reverse transcription-PCR (RT-PCR), nested PCR, and quantitative real-time PCR quantitatively performing the above-mentioned process, performing isothermal gene amplification, or the like, and then performing electrophoresis in a single apparatus. In addition, the present invention relates to an apparatus and method for automatically analyzing biological samples capable of increasing analysis accuracy and efficiency while performing respectively or continuously automatically performing PCR, RT-PCR, nested PCR, and quantitative real-time PCR including the same, isothermal amplification and PCR-electrophoresis, by providing an ultraviolet lamp so as to be moved by a moving part to thereby concentrate radiation on a genetically amplified product so that false-positive by the genetically amplified product may be fundamentally prevented.

BACKGROUND ART

A gene amplification method, which is an in vitro diagnostic testing (IVD testing) technology of amplifying gene having a specific sequence to determine the presence and absence of gene, has been used in various fields such as a food test, a genetically modified organism (GMO) test as well as a pathogenic microorganism test in various animals, plants, or the like, in addition to humans, and a genotype test. In order to perform an accurate gene amplification test from various biological samples, first, a nucleic acid extraction process of removing various reaction inhibitors included in biological samples and inhibiting a gene amplification reaction from the biological samples and obtaining a high purity target nucleic acid is required. Here, the target nucleic acid may be DNA, RNA, or a mixture thereof according to the detection object. The gene amplification test is completed by mixing the target nucleic acid extracted as described above with a gene amplification solution to perform the gene amplification reaction and confirming a DNA corresponding to a DNA length of a genetically amplified product through electrophoresis.

As used herein, the term "biological samples", which are materials from living things, may be interpreted as a meaning including all of materials defined as living things as well as animals, plants, microorganisms, virus, and fungi.

As a method for amplifying DNA in the gene amplification test, a PCR method has been mainly used. In order to detect a trace amount of DNA, a nested PCR method for performing a PCR reaction once more using a complementary primer in a primer base sequence of the amplified DNA has been mainly used. In order to test an expression amount of mRNA of RNA virus or a specific gene, a reverse transcription-PCR (RT-PCR) has been used. In addition, various methods for amplifying DNA or RNA at a predetermined temperature without performing a thermal cycling reaction have been developed.

Meanwhile, since in this PCR method, when DNA amplification is performed in some degree, deoxynucleotide triphosphate is exhausted, such that DNA amplification reaches a limitation point at which amplification may not be performed any more, there is a limitation in quantitative analysis. For example, in the case in which a template nucleic acid has a high initial concentration, the template nucleic acid becomes saturated in a short reaction of 20 cycles or less, and in the case in which a template nucleic acid has an initial concentration of $1/1000$ times the concentration in the above-mentioned case, the template nucleic acid becomes saturated after at least 30 cycles, but after 30 cycles, in both of the cases, detection amounts are the same as each other. In order to solve this problem, a quantitative real-time PCR technology capable of accurately and quantitatively measuring an initial concentration of a nucleic acid by measuring a concentration of the nucleic acid after each of the cycles to measure a cycle at which a concentration of the nucleic acid reaches a predetermined concentration. Since this technology may quantitatively measure a concentration of virus or pathogenic bacteria, this method has been developed as a significantly useful technology in view of molecular diagnosis. In the quantitative real-time PCR technology, methods using fluorescence increased in proportion to an amount of DNA have been mainly used. The fluorescence method as described above is divided into an amplified DNA sequence specific method and an amplified DNA sequence non-specific method. The amplified DNA sequence non-specific method is a method using an intercalating dye binding all of the amplified DNA(s) to increase fluorescence. In case of using this method, an amount of fluorescence is increased in proportion to the amount of all of the amplified DNA(s). Therefore, in the case in which a non-specific amplified product such as a primer-dimer is formed or in the case of amplifying which at least two specific targets, it is impossible to accurately detect an initial amount of the target nucleic acid. On the other hand, in methods using a fluorescent probe specific to an amplified DNA sequence, a plurality of target nucleic acids are amplified in one tube and at the same time, multiplex quantitative detection of nucleic acids may be performed. In this method, since various kinds of probes having different fluorescent properties are selectively hybridized in each of the amplified DNA(s) to thereby exhibit fluorescence while amplifying targets using a pair of primer, a multiplex quantitative real-time PCR method of detecting each of the fluorescent products to quantitatively measuring each of the products has been developed. However, in this method, since as the number of target nucleic acids is increased, a pair of primers and a probe, that is, triple kinds of oligonucleotides should be injected per each target nucleic acid, there was a problem in that in the case of performing the multiplex quantitative real-time PCR on four or more targets, performance may be rapidly decreased. On the other hand, since in a general multiplex PCR, multiplex PCR of ten kinds of target nucleic acids may be optimized so as to be suitably performed, the multiplex PCR may be advantageous for detecting several kinds of target nucleic acid. However, since this PCR method is not quantitative, a method for quantitatively testing a multiplex target has been required. As another limitation of the quantitative real-time PCR method, there was a problem in that since it is impossible to confirm a length of the amplified DNA, it was impossible to use the quantitative real-time PCR method in order to analyze presence or absence of DNA deletion or DNA insertion or detect the number of repeated base such as variable numbers of tandem repeat (VNTR).

In order to solve this problem, an object of the present invention is to provide an automatic apparatus capable of performing quantitative real-time PCR and then confirming a length of the amplified product using a general PCR. Therefore, an object of the present invention is to provide an apparatus capable of simultaneously amplifying various targets, simultaneously and quantitatively each of the targets, and quantitatively measuring an initial amount of DNA in the corresponding target simultaneously with analyzing presence or absence of DNA deletion or DNA insertion or detecting the number of the repeated base such as VNTR.

Meanwhile, since in the gene amplification test, detection may be performed with high sensitivity and specificity, the gene amplification test has been variously used in testing various microorganisms and genes. However, there is an amplicon contamination problem that even though a trace amount of aerosol including the genetically amplified product (amplicon) is contaminated, a false-positive result is obtained due to high sensitivity. In order solve this problem, methods for inactivating the amplified product using ultraviolet rays or an enzyme reaction have been developed. The method using ultraviolet rays is a method for converting a contaminated product into non-amplified DNA by performing an amplification reaction after mixing 8-methoxypsoralene (8-MOP) with a PCR reaction solution in advance, irradiating ultraviolet rays to perform a photochemical reaction with DNA, even in the case in which a PCR product is contaminated later. In the method using an enzyme, which is a method using deoxyuridine triphosphates (dUTP) and uracil deoxy-glycosidase (UDG) enzyme, dUTP is added to a PCR reaction solution, such that a PCR product includes a deoxyuracil base. Then, in this method, the UDG enzyme is added to the PCR product, such that a contaminated PCR product is dissolved and removed through a UDG enzyme reaction before a PCR amplification reaction. However, in the case of the nest PCR in which PCR should be continuously performed using the PCR product, it is impossible to use these methods. Therefore, generally, in an organization performing the gene amplification test, separate laboratories for nucleic acid extraction and purification, preparation of gene amplification reaction sample, and electrophoresis analysis are prepared, respectively, and each of the works is preformed in these laboratories, such that it is costly to prepare and operate the gene amplification laboratories. Nevertheless, since there is still a risk of a false-positive result generated due to contamination by a worker and a false-negative result generated due to an error in nucleic acid extraction and gene amplification reaction solution preparation, a test operation method for preventing the false-positive result and false-negative result is complicated, such that the test is mainly performed in a large hospital and a special clinical test organization.

Therefore, in the gene amplification test, a demand for an economic apparatus for automatically amplifying genes capable of removing the above-mentioned possibility of false-positives and false-negatives and increasing accuracy, reproducibility, and efficiency of the test has been gradually increased.

In order to satisfy the above-mentioned demand, before describing the present invention, each of the steps for performing the gene amplification test according to the related art will be described.

As a method for extracting a nucleic acid from biological samples, in general, a method using magnetic particles has been widely used. This method is a method for rapidly attaching target nucleic acids to fine magnetic particles having a wide surface area in a liquid suspension state, applying a magnetic field to coagulate the magnetic particles including the target nucleic acid attached thereto, removing the filtrate, washing the magnetic particles, eluting pure nucleic acid, and then purifying the nucleic acid, and automation equipments relating to this method have been variously developed.

Recently, an automated method using a pipette has been generally and widely used.

Various methods for separating magnetic particles using a disposable pipette form have been disclosed by Lab system Ltd. as in U.S. Pat. No. 5,647,994. This method is a related art relating to a method for coagulating magnetic particles in a pipette as in U.S. Pat. No. 5,702,950 or 6,187,270. The apparatus using the disposable pipette is composed of a component having a single tube shape, connected in series to a zet channel that is defined as a distal flow gate of the tube, and having a diameter smaller than that of a separation chamber; a magnetic component positioned at a first position adjacent to an outside of a separation wall or a second position in the separation chamber and arranged so that when the magnetic component is positioned at the first position, magnetic particles may be collected by an influence of a magnetic field, and when the magnetic component is positioned at the second position, it is impossible to catch the magnetic particles any more; and a tube, which is second portion connected in series to the separation chamber having a cylindrical shape and separated from the zet channel, having a structure in which a cylinder channel is equipped with a movable piston to thereby suck and discharge a liquid.

In addition, various purification apparatuses using a pipette and a magnetic property have been suggested.

However, in the cases of all of the structures as described above, a method capable of separating a target nucleic acid from a solution using a disposable pipette to suspend the separated target nucleic acid in a different solution has been suggested, but these structure have a large limitation in that nucleic acid extraction may be frequently unsuccessful due to a blocking phenomenon generated at a lower end portion of the pipette by magnetic particles.

Further, there are problems in that since a serial process of separating the target nucleic acid from a biochemical mixture solution is performed in the pipette, uniform suspension of the solution is difficult, and after the washing corresponding to a final step of purification is completed, since a washing solution is not completely removed but a residual washing solution is included at the time of elution, a subsequent gene amplification process, or the like, may be affected by the residual washing solution.

In the performing of the gene amplification reaction from the extracted target nucleic acid, various methods such as PCR, nested PCR, RT-PCR, isothermal nucleic acid amplification method, and the like, have been developed in order to amplify the target nucleic acid. Generally, a preparation step of mixing an extracted target nucleic acid with a gene amplification reaction solution to prepare a gene amplification reactant and a reaction step of performing a reaction are required. In the preparation step of mixing a gene amplification reaction solution containing a primer, nucleic acid polymerase, a nucleotide triphosphate dNTP or NTP, which is a polymerization monomer, and a buffer with the extracted target nucleic acid at a predetermined amount to prepare the reaction. In the gene amplification reaction step, in the case of isothermal amplification, there is a need only to maintain a predetermined temperature, but in the case of using PCR, a heating and cooling step for a thermal cycling reaction is required. Since a temperature should be increased in order to perform the gene amplification reaction, generally, sealing is performed in order to prevent evaporation. However, in the case of sealing a gene amplification reaction vessel, the sealed vessel should be opened and the genetically amplified product should be transferred to an electrophoresis gel 362 in order to perform an electrophoresis analysis on the genetically amplified product after gene amplification reaction, but there are problems in that a complicated apparatus for automatically performing the process as described above is required, and the genetically amplified product may be contaminated. Particularly, in the case of nested PCR, since it is impossible to use an inactivation method of the amplified product for preventing contamination of the amplified product, the nest PCR depends on a space separation for performing the test.

In a process of analyzing the genetically amplified product through the electrophoresis, generally, an agarose electrophoresis method has been used. This method, which is a traditional method, has advantages such as a cheap cost, and simple analysis, but there are problems in that an analysis time is relatively long, and a lot of manual work of those skilled in the art should be performed. Recently, in order to solve this problem, methods using a capillary electrophoresis capable of rapidly and automatically performing electrophoresis have been developed, but an apparatus and supplies are expensive, such that these methods have been restrictively used. Since in all of the electrophoresis steps, analysis is always performed using the genetically amplified product, there is a problem in that fine aerosol generated therefrom may be mixed again with the gene amplification reaction solution to cause false-positives. Therefore, a method capable of preventing this problem is required.

Various apparatuses are developed for quantitative real-time PCR. However, most of the apparatuses are complicated and expensive. In addition, an apparatus capable of continuously and automatically performing the quantitative real-time PCR as in a general PCR reaction has not been developed, such that a simple and convenient apparatus and method capable of continuously performing this process have been required.

In performing the entire process of nucleic acid extraction, quantitative real-time PCR/PCR, and electrophoresis as described above, an apparatus and method for automatically analyzing biological samples capable of preventing contamination by external and internal contamination factors, having high reliability, increasing convenience, reproducibility, and efficiency, and having excellent test accuracy by automating the entire process required for analysis while continuously performing quantitative real-time PCR and general PCR have been required.

DISCLOSURE

Technical Problem

An object of the present invention is to provide a convenient, reproducible, and economical gene test system capable of automatically performing PCR, nested PCR, RT-PCR, and quantitative real-time PCR quantitatively performing the above-mentioned process, a isothermal gene amplification process, and the like, by automatically performing a complicated process of purifying a target nucleic acid from biological samples, and amplifying and analyzing the purified target nucleic acid using a single apparatus. Another object of the present invention is to provide an apparatus and method for automatically analyzing biological samples capable of having excellent accuracy by solving an inveterate false-positive problem generated in a repetitive test and preventing contamination of a test specimen.

Technical Solution

In one general aspect, an apparatus for automatically analyzing biological samples includes: a case 100 including an opening part 110 formed so as to open a predetermined region; a purification part 200 including a multi-well plate kit 210 in which a plurality of wells 211 form first to N-th rows and wells in a specific row among the first to N-th rows are embedded with biological samples, one or more samples or reagents required for purification to purify a target nucleic acid from the biological samples; a nucleic acid amplification part 400 amplifying the target nucleic acid purified by the purification part 200; an electrophoresis part 300 including an electrophoresis body 310 to inspect an amplified product through the nucleic acid amplification part 400; a plurality of pipettes 500 forming rows and moving the biological samples, the sample or reagent used in the purification part 200, the purified target nucleic acid, and amplified DNA; a moving part 600 moving the pipettes 500 in length and height directions of the case 100 and adjusting an operation of the pipettes 500; and a control part (not shown) controlling the purification part 200, the nucleic acid amplification part 400, the electrophoresis part 300, and the moving part 600.

The apparatus 1000 for automatically analyzing biological samples may further include a base plate 700 including the multi-well plate kit 210 and the electrophoresis body 310 that are detachably provided therein and guided by a guide part 130 fixed to a lower surface of the case 100 to be movable through the opening part 110 in the length direction of the case 100.

The apparatus 1000 for automatically analyzing biological samples may further include a first sterilization unit 800 fixed to the moving part 600.

The first sterilization unit 800 may be an ultraviolet lamp and may further include a reflection unit 810.

The purification part 200 may include: a magnetic field application part 201 including a magnet 221 to apply a magnetic field to wells in a specific row in the multi-well plate kit 210; and a heating part 202 formed adjacent to the magnetic field application part 201 to heat the wells in the same specific row.

The purification part 200 may further include a biological sample tube rack 280 including biological sample tubes 281 putting the biological samples for extracting the target nucleic acid, wherein the biological sample tube rack 280 is detachably provided in the base plate 700.

The magnetic field application part 201 may include: a magnet mounting part 220 on which the magnet 221 is mounted; and a lift part 270 mounted on the lower surface of the case 100 to lift up and down the magnet mounting part 220.

One or more samples or reagents required for purification, embedded in wells in the first to N-th rows in the multi-well plate kit 210 may include one or more of an enzyme, a cell lysate solution, a nucleic acid binding solution, an aqueous dispersion of magnetic particles, and a washing solution.

An insertion groove 222 may be formed in a surface of the magnet mounting part 220 on which the magnet 221 is mounted so that a lower portion of a specific row in the multi-well plate kit 210 is inserted, and the base plate 700 may be formed with a first exposure hole 701 at which a predetermined region is hollow so that the lower portion of the specific row is seated in the insertion groove 222 at the time of lifting up the magnet mounting part 220.

The magnet mounting part 220 may be made of a metal material, and the heating part 202 may be a heat generation film formed to contact with the magnet mounting part 220.

In the base plate 700, a protrusion fixing part 730 protruding from a lower portion of the multi-well plate kit 210 so as to be positioned between the plurality of wells 211 and an elastic unit 731 provided on the protrusion fixing part 730 to thereby be closely adhered to the well 211 may be further formed.

In the base plate 700, a waste liquid vessel 740 storing waste liquids discarded after being used may be detachably provided.

In the apparatus 1000 for automatically analyzing biological samples, the moving part 600 may include a pipette block 630 capable of mounting and detaching the pipettes 500, and a pipette rack 510 capable of storing the pipettes 500 may be detachably provided in the base plate 700.

In the pipette block 630 of the moving part 600, a pipette fixing protrusion part 644-1 of which the pipette 500 is mounted on a lower portion may be formed, and the pipette 500 may be mounted on the pipette fixing protrusion part 644-1 through a pipette mounting part including a pipette block fixing plate 644 being movable in the height direction.

In the pipette block 630 of the moving part 600, suction and discharge of the pipette 500 may be adjusted by a pipette adjusting part including pistons 631 formed at an upper portion thereof and a piston fixing plate 634 including the pistons 631 fixed thereto and being movable in the height direction.

The pipette block 630 of the moving part 600 may include: a pipette extrusion plate 638-1 having a hollow region corresponding to the pipette fixing protrusion part 644-1 and positioned so as to contact between a lower surface of the pipette block fixing plate 644 and an upper surface of the pipette 500 when the pipette 500 is mounted, a pipette extrusion pin fixing plate 639 positioned over the pipette block 630, and pipette extrusion pins having a length longer than a height of the pipette block 630 and connecting the pipette extrusion plate 638-1 and the pipette extrusion pin 638 fixing plate 639 to each other, wherein when the pipette extrusion pin fixing plate 639 is moved downwardly by an operation of the pipette adjusting part, the pipette extrusion pin fixing plate 639, the pipette extrusion pins 638-1, and the pipette extrusion plate 638-1 are moved downwardly, and the pipette 500 is detached from the pipette fixing protrusion part 644-1.

The purification part 200 may further include a drying part 290 including a vacuum module 291 capable of being detached from/attached to the moving part 600, a vacuum module rack 293 mounted on an inner lower surface of the case 100 to store the vacuum module 291 at a predetermined position, and a vacuum pump 295 connected to the vacuum module 291 through a hose.

In the drying part 290, a convex part 294 may be formed to protrude from an upper surface of the vacuum module rack 293, and a concave part 292 corresponding to the convex part 294 may be formed at a lower surface of the vacuum module 291.

In the drying part 290, a support part 293-1 supporting one portion of the vacuum module 291 may be provided at the vacuum module rack 293, and a magnet may be embedded at surfaces of the support part 293-1 and the vacuum module 291 contacting with each other.

The electrophoresis part 300 may include: the electrophoresis body 310 seated on an electrophoresis body fixing plate 750 installed at the base plate 700 and formed with hole type electricity connection terminals 311 connected to electrode lines 311a forming positive and negative electrodes, respectively; a protrusion type electricity connection terminal 341 inserted into the hole type electricity connection terminal 311 of the electrophoresis body 310 for connecting power; a power supply part 320 fixed to an inner surface of a lower portion of the case 100 to supply power to the electrophoresis body 310; an excitation light irradiation part 330 irradiating excitation light to the electrophoresis body 310; and a photographing part 350 photographing a state of electrophoresis.

In the electrophoresis part 300, as the base plate 700 is inserted into the case 100, a first contact part 342 and a second contact part 322 contacting with and connected to each other may be formed to be inclined at a lower surface of a power connection terminal 340 and an upper surface of the power supply part 320, and closely adhered to each other by an elastic unit 321 at a lower portion of the second contact part 322 of the power supply part 320.

In the excitation light irradiation part 330, light emitting diodes (LEDs) irradiating light in an excitation light wavelength band toward the electrophoresis body 310 may be arranged and provided on an inner lower surface of the case 100 at equidistance, the electrophoresis body fixing plate 750 of the base plate 700 on which the electrophoresis body 310 is seated may be made of a material scattering the excitation light, and a bottom plate of the electrophoresis body 310 may be made of a material absorbing light in a fluorescence wavelength band of the nucleic acid and passing the light in an excitation light wavelength band.

The photographing part 350 may be formed to include an image sensor, a lens, and a short wavelength filter and fixed to a moving part body 610 of the moving part 600.

The electrophoresis part 300 may further include a marker storage part 900 including marker tubes 920 embedded with a marker and a fluorescent dye material and a marker tube rack 910 mounted with the marker tubes 920, wherein the marker tube rack 910 is detachably provided in the base plate 700.

The electrophoresis body 310 may further include a gel tray 360 or 360-1, wherein the gel tray 360 or 360-1 includes an electrophoresis loading well 363 formed at a bottom thereof and a plurality of electrophoresis gel fixing part 361 formed at position that is not overlapped with an electrophoresis moving path.

The nucleic acid amplification part 400 may include: amplification tubes 411 forming one or more rows; an amplification block 410-1 formed with concave seating grooves 421 closely adhered to a lower portion thereof and made of a metal into which a temperature sensor is inserted; an amplification block cover 410 made of a heat insulation material provided with a first fixed magnet 422; a peltier element 423; a heat transferring part 420 transferring heat generated in the peltier element 423 to the outside; and an amplification tube fixing part 430 formed with holes smaller than an upper surface of the amplification tube 411, formed so as to enclose a predetermined region of an upper portion of the amplification tube 411, including a second fixed magnet 431 inserted thereinto so as to correspond to the first fixed magnet 422 and fix the amplification tube 411, and having a height spaced apart from a surface on which the amplification block cover 410 is formed by a predetermined distance.

In the base plate 700, a hollow second exposure hole 702 may be formed so that the amplification block 410-1 and the amplification tube fixing part 430 correspond to the amplification tube fixing part 430.

The nucleic acid amplification part 400 may be positioned adjacently to the opening part 110.

The nucleic acid amplification part 400 may further include: a light irradiation part 440 irradiating fluorescent excitation light toward the amplification tube 411; and a fluorescence detector 450 provided movably in a vertical direction so as to be closely adhered to the upper portion of the amplification tube 411 to real-time measure an amount of fluorescence in the amplification tube 411.

In the base plate 700, a handle 710 may be formed at an upper surface of one portion adjacent to the opening part 110.

The case 100 may further include an air flow part 142 forming a channel through which air flows at an outer lower surface thereof and an air blower 141 blowing air to the air flow part 142.

In the apparatus 1000 for automatically analyzing biological samples, a first position fixing part 720 may be further formed at an end portion of the other portion of the base plate 700; and a second position fixing part 120 fixed to the case 100 may be further formed at a position corresponding to the first position fixing part 720, wherein the first and second position fixing parts 720 and 120 are fixed to each other by magnetism of a third fixed magnet 721.

In another general aspect, a method for automatically analyzing biological samples using the apparatus 1000 for automatically analyzing biological samples as described above may include: a purification step (S10) of obtaining a target nucleic acid from the biological sample; an amplification step (S20) of amplifying the target nucleic acid purified in the purification step (S10); and an electrophoresis step (S30).

The method for automatically analyzing biological samples may further include, before the purification step (S10), a preparation step (S40) including a first mounting step of taking out the base plate 700 to the outside of the case 100 and mounting the electrophoresis body 310, the pipette rack 510, the multi-well plate kit 210, the biological sample tube rack 280, the waste liquid vessel 740, the marker tube rack 910, and the marker tube 920 of the base plate 700; an inserting step of inserting the base plate 700 so that the first position fixing part 720 and the second position fixing part 120 contact with each other to thereby be fixed to each other; and a second mounting step of seating the amplification tube 411 on the amplification block 410-1 exposed by the second exposure hole 702 of the base plate 700 and fixing the amplification tube 411 by the first fixed magnet 423 of the amplification block cover 410 and the second fixed magnet 431 of the amplification tube fixing part 430.

The purification step (S10) may include: a pipette mounting step of moving the moving part 600 to insert pipettes 500 into the pipette block 630; and a target nucleic acid containing solution obtaining step of moving the moving part 600 to transfer/mix the biological samples and one or more samples or reagents for purification respectively embedded in the wells in the first to N-th rows of the multi-well plate kit 210 to obtain the target nucleic acid containing solution that is a mixture in which the magnetic particles are excluded, and if necessary, a magnetic field applying step of applying a magnetic field to wells in a specific row of the multi-well plate kit 210 by the magnetic field application part 201 and a heat step of heating the wells in the specific row of the multi-well plate kit 210 by the heating part 202 may be further performed.

The target nucleic acid containing solution obtaining step may include: a sample dissolving step of dissolving the biological sample to elute a nucleic acid in the purification part 200; a target nucleic acid attaching step of attaching the target nucleic acid to magnetic particles and removing the remaining solution; a magnetic particle washing step of washing the magnet particles to which the target nucleic acid is attached to remove impurities; a magnetic particle drying step of detaching the pipette 500 mounted on the moving part body 610, fixing the vacuum module 291 to the moving part body 610 of the moving part 600, and sucking a washing solvent in wells in the specific row in the multi-well plate kit 210 to dry the magnetic particles; and an obtaining step of adding an elution buffer to the dried magnetic particles to obtain the target nucleic acid.

The amplification step (S20) may include: a mixing step of moving the target nucleic acid containing solution obtained through the purification step (S10) to the amplification tube 411 to perform the mixing; and a temperature regulating step of regulating a temperature by the heat transferring part 420 to perform amplification.

The electrophoresis step (S30) may include: a marker mixing step of mixing an amplified product and a marker solution with each other; an electrophoresis performing step of supplying power to the electrophoresis body 310 by the power supply part 320 and the power connection terminal 340 to separate the amplified product; and an analyzing step of irradiating light by the excitation light irradiation part 330, measuring an electrophoresis pattern of the amplified product using the photographing part 350, and analyzing a molecular weight.

The method for automatically analyzing biological samples may further include, between the amplification step (S20) and the electrophoresis step (S30), an inactivation step (S50) of operating the first sterilization unit 800 to inactivate the amplified nucleic acid.

In the amplification step (S20), quantitative real-time amplification analysis of calculating an initial concentration of the nucleic acid may be performed by measuring an amount of fluorescence generated for a predetermined time or per cycle while irradiating a predetermined amount of excitation light using the fluorescence detector 450 through a light irradiation part 440 to detect a timing at which a critical fluorescent value is detected.

In the method for automatically analyzing biological samples, a quantitative amplification analysis value obtained in the amplification step (S20) may be corrected and analyzed through results including the molecular weight and the number of amplified product obtained through the electrophoresis step (S30).

In another general aspect, a method for getting a concentration of an antigen using quantitative immuno-PCR may be characterized in that a concentration of an antigen contained in biological samples is quantitatively inspected by performing quantitative immuno-PCR using the apparatus 1000 for automatically analyzing biological samples as described above.

Advantageous Effects

As described above, the apparatus and method for automatically analyzing biological samples according to the present invention are apparatus and method for purifying, amplifying, and analyzing the target nucleic acid from the biological samples. According to the present invention, various gene amplification analysis such as PCR, Nested PCR, RT-PCR, and quantitative real-time PCR including the above-mentioned reactions, isothermal nucleic acid amplification, and the like, may be automatically and efficiently performed in the single apparatus, and the system capable of preventing contamination may be provided, thereby making it possible to increase analysis accuracy.

Particularly, in the apparatus and method for automatically analyzing biological samples according to the present invention, the nucleic acid may be quantitatively analyzed through the quantitative real-time PCR, and the length of the amplified DNA may be analyzed by subsequently performing electrophoresis, such that there is an advantage in that VNTR, gene insertion, deletion, and mutation, and the like, may be quantitatively analyzed. This advantage may be applied to various diagnosis fields. As an example, a lot of cost and time are consumed to test a concentration of virus in blood using quantitative PCR and testing virus mutants through a gene sequence determining test in order to treat various viral diseases. In the case of using the apparatus according to the present invention, a quantitative test and a mutation test of a virus may be performed at once by performing quantitative real-time PCR using a multiplex PCR tube containing pairs of primers designed so that PCR products selective to each of the mutants and having different lengths are formed to measure fluorescence values capable of quantifying the virus, and then performing electrophoresis on the reactants to measure lengths of amplified DNA. Since all of the operations as described above are automatically performed, there is an advantage in that the quantitative test and the mutation test of the virus may be simply and rapidly performed using a single clinical sample.

Further, in the apparatus and method for automatically analyzing biological samples according to the present invention, the ultraviolet lamp is movably provided at the moving part, such that the genetically amplified product may be inactivated immediately after gene amplification, thereby making it possible to prevent false-positive results caused by contamination of the genetically amplified product. In order to prevent an apparatus from being contaminated by pathogenic bacteria included in the biological samples, the sterilization unit for entire sterilization may be further provided, and all of the processes are performed in the case, such that a contamination source from the outside may be blocked, thereby further increasing reliability of the analysis.

Further, in the apparatus and method for automatically analyzing biological materials according to the present invention, the multi-well plate kit, the waste liquid vessel, the electrophoresis body, the biological sample tube rack, the pipette rack, and the marker tube rack are detachably formed in the base plate, such that it is easy to mount each of the modules, and analysis may be prepared by a simple method of mounting and inserting each of the components.

Furthermore, in the apparatus and method for automatically analyzing biological samples according to the present invention, in the case in which the magnet mounting part is made of the metal material and the heating part is the unit heating the magnet mounting part, magnetic field application and the heating may be simultaneously performed on wells in a specific row, such that purification efficiency may be further increased.

In addition, in the apparatus and method for automatically analyzing biological samples according to the present invention, the drying part is provided, the remaining solvent may be rapidly removed in order to prevent the washing solvent from being remained in the purified target nucleic acid solution to have a negative influence on the amplification in advance. Particularly, as the moving part body is used for detachment and movement of the vacuum module of the drying part, the configuration of the entire apparatus may be simplified, and the operation may become easy.

Further, in the apparatus and method for automatically analyzing biological samples according to the present invention, the seating groove on which the amplification tube is seated is formed on the upper surface of the temperature regulating unit, and the fixing part is formed so as to be supported by the upper portion of the amplification tube to enclose the amplification tube, such that the amplification tube may be stably fixed, and the change in the temperature may be prevented, thereby making it possible to increase amplification efficiency.

Further, in the apparatus and method for automatically analyzing biological samples according to the present invention, the photographing part is fixed to the moving part, such that the photographing distance may be decreased, thereby making it possible to obtain a precise electrophoresis image with high sensitivity.

In addition, in the apparatus and method for automatically analyzing biological samples according to the present invention, as the first and second position fixing parts are formed, the base plate may be simply fixed, and at the time of inserting the base plate, the first inclined part of the power connection terminal and the second inclined part of the power supply part contact with each other to thereby be guided, the elastic unit is compressed, and the first contact part of the power connection terminal and the second contact part of the power supply part may contact with each other at the final insertion position of the base plate, such that the electrophoresis part may be easily operated.

In the apparatus and method for automatically analyzing biological samples according to the present invention, the lower surface of the case is used as a heat radiating plate, and the air flow part and the air blower are formed, such that the lower surface of the case may be suitably cooled, thereby making it possible to efficiently use a peltier cooling element.

DESCRIPTION OF DRAWINGS

FIGS. 1 and 2 are a perspective view and a bottom perspective view showing an apparatus for automatically analyzing biological samples according to the present invention.

FIGS. 3 and 4 are perspective views of the apparatus for automatically analyzing biological samples according to the present invention, respectively (FIG. 3 shows a state in which an outer cover of a case is removed, and FIG. 4 shows a state in which the outer cover and a backbone are partially removed).

FIG. 5 is a view showing a moving part body and a moving part of the apparatus for automatically analyzing biological samples according to the present invention.

FIGS. 6 to 8 are views showing a pipette mounting operation, a suction and discharge adjusting operation, and a detachment operation of the apparatus for automatically analyzing biological samples according to the present invention, respectively.

FIG. 9 is a view showing a separation state of a base plate of the apparatus for automatically analyzing biological samples according to the present invention.

FIGS. 10 and 11 are an assembly perspective view and an exploded perspective view of an upper portion of the base plate of the apparatus for automatically analyzing biological samples according to the present invention.

FIG. 12 is an exploded perspective view showing a fixation state of the base plate and a multi-well plate kit of the apparatus for automatically analyzing biological samples according to the present invention.

FIGS. 13 and 14 are a perspective view and a bottom perspective view showing a magnetic field application part and a heating part of the apparatus for automatically analyzing biological samples according to the present invention.

FIGS. 15 to 16B are views showing a drying part of the apparatus for automatically analyzing biological samples according to the present invention.

FIG. 17 is a view for describing use of the drying part of the apparatus for automatically analyzing biological samples according to the present invention.

FIGS. 18 and 19 are a perspective view and a cross-sectional view showing a nucleic acid amplification part for real-time nucleic acid amplification of the apparatus for automatically analyzing biological samples according to the present invention.

FIGS. 20 and 21 are other views showing the nucleic acid amplification part of the apparatus for automatically analyzing biological samples according to the present invention.

FIGS. 22 and 23 are views showing an electrophoresis part of the apparatus for automatically analyzing biological samples according to the present invention, respectively.

FIG. 24(*a*) and FIG. 24(*b*) are views showing a shape in which the electrophoresis part of the apparatus for automatically analyzing biological samples according to the present invention is electrically connected.

FIGS. 25 and 26 are views showing a method for automatically analyzing biological samples according to the present invention.

DETAILED DESCRIPTION OF MAIN ELEMENTS

1000: apparatus for automatically analyzing biological sample
100: case
110: opening part
120: second position fixing part
130: guide part
140: bottom surface of case
141: air blower
142: air flow part
150: support bar
200: purification part
201: magnetic field application part
202: heating part
210: multi-well plate kit
211: well
220: magnet mounting part
221: magnet
222: insertion groove
230: magnet mounting part supporter
240: guide bar
250: guide block
260: extension spring
270: lift part
271: lift motor
272: first lift shaft
273: lift cam
274: second lift shaft
275: height sensing sensor
275-1: sensing part
275-2: sensing target part
280: biological sample tube rack
281: biological sample tube
290: drying part
291: vacuum module
292: concave part
293: vacuum module rack
293-1: support part
294: convex part
295: vacuum pump
296: fixed magnet
300: electrophoresis part
310: electrophoresis body
311: hole type electricity connection terminal
320: power supply part
321: elastic unit
322: second contact part
323: second inclined part
330: excitation light irradiation part
340: power connection terminal
341: protrusion part
342: first contact part
343: first inclined part
350: photographing part
360, 360-1: gel tray
361: electrophoresis gel fixing part
362: electrophoresis gel
363: loading well
400: nucleic acid amplification part
410: amplification block cover
410-1: amplification block
411: amplification tube
420: heat transferring part
421: seating groove
422: first fixed magnet
423: peltier element
430: amplification tube fixing part
431: second fixed magnet
440: light irradiation part
450: fluorescence detector
500: pipette
510: pipette rack
600: moving part
610: moving part body
621: slider
622: X axis moving motor
623: X axis moving belt
630: pipette block
631: piston
632: piston motor
633: piston belt
634: piston fixing plate
635: piston moving screw
636: piston moving screw nut
637: piston guide bar
638: pipette extrusion pin
638-1: pipette extrusion plate
639: pipette extrusion pin fixing plate
641: Z axis screw
642: Z axis motor
643: Z axis moving belt
644: pipette block fixing plate
644-1: pipette fixing protrusion part
645: Z axis screw nut
646: Z axis guide bar
647: Z axis guide bar slide
700: base plate
701: first exposure hole
702: second exposure hole
710: handle
720: first position fixing part
721: third fixed magnet
730: protrusion fixing part
731: elastic unit
740: waste liquid vessel
750: electrophoresis body fixing plate
800: first sterilization unit 810: reflection unit
820: second sterilization unit
900: marker storage part
910: marker tube rack
920: marker tube

BEST MODE

Hereinafter, an apparatus 1000 and method for automatically analyzing biological sample according to the present invention having the above-mentioned characteristics will be described in more detail with reference to the accompanying drawings.

The apparatus 1000 for automatically analyzing biological samples is formed to include a case 100; a purification part 200 purifying a target nucleic acid from the biological samples; a nucleic acid amplification part 400 amplifying the target nucleic acid purified by the purification part 200; an electrophoresis part 300 including an electrophoresis body 310 to inspect an amplified product through the nucleic acid amplification part 400; pipettes 500 moving a sample or a reagent used in the purification part 200, the purified target nucleic acid, and the amplified target nucleic acid; a moving part 600 adjusting an operation of the pipette 500 and moving the pipette 500 in length and height directions of the case 100; a first sterilization unit 800, and a control part (not shown).

The case 100, which is a basic body configuring the apparatus 1000 for automatically analyzing biological sample according to the present invention may be formed to include a backbone and an outer cover.

The case 100 is shown in some of the accompanying drawings of the present invention, in a state in which the case 100 is partially removed in order to more easily describe components provided in the case 100.

An opening part 110 capable of opening and closing a predetermined region is formed in the case 100 so that a base plate 700 may be take out and inserted in the length direction of the case 100.

The base plate 700, which may be added to the apparatus 1000 for automatically analyzing biological samples according to the present invention, will be described below again.

The case in which the opening part 110 is formed so that a predetermined region of a left side surface of the case 100 is opened and closed is shown by way of example in FIG. 1. In this case, the opening part 110 needs to be formed at a size at which the base plate 700 may be take out when the opening part 110 is opened.

The case 100 is positioned so as to be spaced apart from a ground on which an outer lower surface is mounted by a predetermined distance, and the outer lower surface of the case 110 may be further provided with an air flow part 142 forming a channel in which air flows and an air blower 141 blowing air to the air flow part 142.

The air flow part 142 may be formed so that a plurality of heat radiation pins formed to be long in the length direction of the case 100 are densely provided to form a plurality of air channels.

The air blower 141 is a component blowing air to the air flow part 142.

In the apparatus 1000 for automatically analyzing biological samples according to the present invention, the air flow part 142 and the air blower 141 are formed, such that the lower surface of the case 100 may be efficiently cooled, and in order to increase cooling efficiency, the lower surface of the case 100 may be made of a material having high thermal conductivity (for example, an aluminum material).

The purification part 200 is a component purifying the target nucleic acid from the biological samples.

The purification part 200 includes a multi-well plate kit 210, a magnetic field application part 201, and a heating part 202. In the multi-well plate kit 210, a plurality of wells 211 form first to N-th rows of wells, but the biological sample and one or more samples or reagents required for purification are embedded in each of the wells in a specific row among the first to N-th rows. More specifically, in the multi-well plate kit 210, the plurality of wells 211 provided in a horizontal direction form a plurality of rows, and the biological sample and one or more samples or reagents required for purification are embedded in each of the wells in the first to N-th rows. In more detail, the sample or reagent required for purification may include an enzyme, a cell lysate solution, a nucleic acid binding solution, an aqueous dispersion of magnetic particles, and a washing solution. In this case, wells in some rows in the multi-well plate kit 210 may be empty.

The multi-well plate kit 210 is detachably provided in the base plate 700 in a state in which the biological samples and the reagent or sample required for purification are embedded therein, such that a user needs not to perform a separate process without mounting the multi-well plate kit 210 for purification. Therefore, the apparatus 1000 for automatically analyzing biological sample may be conveniently used.

The magnetic field application part 201 includes magnets 221 and applies a magnetic field to wells in a specific row in the multi-well plate kit 210 to thereby serve to separate magnetic particles from the solution to which the target nucleic acid is attached. Further, the purification part 200 may include the heating part 202 to further increase purification efficiency by accelerating various reactions. The heating part 202 is a component formed adjacent to the magnetic field application part 201 to heat wells in the same specific row. The same specific row means a row selected from the first to N-th rows formed in the multi-well plate kit 210, and the magnetic field application part 201 and the heating part 202 may respectively apply a magnetic field to the wells in the specific row, or simultaneously apply the magnetic field and heat thereto. In this case, application of the magnetic field is performed by a lift part 270 lifting up and down a magnet mounting part 220 on which the magnets 221 are mounted, and in order to increase magnetic field application efficiency and heat transferring efficiency at the time of heating, an insertion groove 222 in which lower portions of wells in a specific row are seated may be formed in the magnet mounting part 220.

A first exposure hole 701 in which a predetermined region is hollow needs to be formed at a portion of the base plate 700 on which a specific row in the multi-well plate kit 210 is positioned so that wells in the specific row may be directly seated in the insertion groove 222 of the magnetic field application part 201.

The heating part 202 may have various shapes as long as it may heat wells in a specific row, but the magnet mounting part 220 may be made of a metal material, and the heating part 202 may be a unit heating the magnet mounting part 220 and use a heat generation film.

In the apparatus 1000 for automatically analyzing biological samples according to the present invention, in the case in which the magnet mounting part 220 is made of the metal material and the heating part 202 is the unit heating the magnet mounting part 220, magnetic field application and the heating may be simultaneously performed on the wells in the specific row, such that purification efficiency may be further increased.

The lift part 270, which is a component mounted in the lower surface of the case 100 to lift up and down the magnet mounting part 220, may be variously formed, and an example of the lift part 270 shown in FIGS. 13 and 14 will be described.

The lift part 270 may include a lift motor 271; a first lift shaft 272 having one end portion connected to the lift motor 271 to rotate; a lift cam 273 integrally connected to the other end portion of the first lift shaft 272; and a second lift shaft 274 having one end portion connected to the lift cam 273 so as to be movable in a height (vertical) direction while circularly moving at the time of rotation of the lift cam 273.

Further, the magnetic field application part 201 may include a magnet mounting part supporter 230 supporting the magnet mounting part 220, and a guide bar 240 may be connected to a lower surface of the magnet mounting part supporter 230.

The guide bar 240 is inserted into a guide hole of a guide block 250 including the guide hole formed so as that the guide bar is slid in the height direction.

Here, an extension spring 260 may be provided between the magnet mounting part 220 and the supporter, such that the magnet mounting part 220 may be stably seated on the multi-well plate kit 210.

The shape of the lift part 270 is only an example, and the apparatus 1000 for automatically analyzing biological sample according to the present invention is not limited thereto.

The pipette 500 is mounted on a moving part body 610 moved and operated by the moving part 600, and the biological samples and the samples or reagent required for purification that are embedded in the multi-well plate kit 210 are transferred by suction and discharge of the pipette 500 to thereby be mixed in the purification part 200. During the above-mentioned process, the magnetic field is applied by the magnetic field application part 201, and the heating is performed by the heating part 202, thereby performing purification.

(A detailed configuration example of the moving part 600 will be described below again.)

The lift part 270 may be operated together with a height sensing sensor 275 including a sensing part 275-1 and a sensing target part 275-2.

In addition, the purification part 200 may further include a biological sample tube rack 280 including biological sample tubes 281 putting the biological samples for extracting the target nucleic acid, and it is preferable that the biological sample tube rack 280 is detachably formed in the base plate 700 so as to be easily transferred.

In the apparatus 1000 for automatically analyzing biological samples according to the present invention, the magnetic field application part 201 and the heating part 202 may be positioned adjacently to the plurality of wells 211 while being moved by the lift part 270 in the height direction in order to perform a process of applying the magnetic field and heat to the multi-well plate kit 210 in the purification part 200. In this case, in order to stably fix the multi-well plate kit 210 to the base plate 700, a protrusion fixing part 730 protruding so as to be positioned between the plurality of wells 211 and an elastic unit 731 provided on the protrusion fixing part 730 to thereby be closely adhered to the wells 211 may be further formed in the base plate 700 on which the multi-well plate kit 210 is seated.

The elastic unit 731, which is a component fixed to the protrusion fixing part 730, is made of a material providing friction force such as a rubber ring to thereby stably fix the multi-well plate kit 210.

In the apparatus 1000 for automatically analyzing biological samples according to the present invention, when the base plate 700 is fixed to a specific position, the multi-well plate kit 210 is also fixed to an accurate position, such that it is easy to control the moving part 600. Therefore, the apparatus 1000 for automatically analyzing biological samples has an advantage in that purification may be easily performed.

In the apparatus 1000 for automatically analyzing biological samples according to the present invention, the pipette 500 may be detachably provided at the moving part body 610 of the moving part 600 and the pipette 500 is replaced after a single analysis is completed or reused after washing. In order to this process, the pipette rack 510 capable of storing the pipettes 500 may be provided.

In this case, it is preferable that the pipette rack 510 provided with the pipette 500 is mounted on the base plate 700 at the time of taking out the base plate 700 and inserted into the case 100, and the pipette 500 is fixedly moved/operated so that the pipette 500 may be attached to and detached from the moving part body 610 of the moving part 600.

That is, it is preferable that the pipette rack 510 fixing the pipette 500 is detachably mounted on the base plate 700.

In addition, a drying part 290 exhausting air of wells in a specific row in the multi-well plate kit 210 may be further formed in the purification part 200 in order to increase washing efficiency (see FIGS. 15 to 17), and the pipette rack 510 stores the pipettes 500 when the moving part 600 performs a work relating to an operation of the drying part 290.

The drying part 290 is formed to include a vacuum module 291, a vacuum module rack 293 mounted on an inner lower surface of the case 100 to store the vacuum module 291 at a predetermined position, and a vacuum pump 295 connected to the vacuum module 291 through a hose. The vacuum module rack 293 is a component storing the vacuum module 291 at the predetermined position when the vacuum module 291 is not used. A convex part 294 is formed to protrude from an upper surface of the vacuum module rack 293, and a concave part 292 corresponding to the convex part 294 is formed at a lower surface of the vacuum module 291, such that the vacuum module 291 may be easily stored at the accurate position of the vacuum module rack 293. In this case, it is preferable that the convex part 294 is formed to have a diameter increased downwardly to thereby be inclined so that the vacuum module 291 may be easily seated.

Additionally, in the drying part 290, a support part 293-1 supporting one portion of the vacuum module 291 may be further provided at the vacuum module rack 293 in order to further maximize an effect of preventing movement of the vacuum module 291, and a fixed magnet 296 may be embedded at surfaces at which the support part 293-1 and the vacuum module 291 contact with each other.

FIG. 16A shows a lower portion of the vacuum module 291, and FIG. 16B shows the vacuum module rack 293.

Holes are formed in an upper portion of the vacuum module 291 so as to be attached to and detached from the moving part body 610 of the moving part 600, such that in the case in which vacuum drying is required, the moving part body 610 of the moving part 600 moves to an accurate position of the vacuum module rack 293 to attach the vacuum module 291 and moves to a specific row in the multi-well plate kit 210, and the vacuum module 291 exhausts air of the wells in the specific row by an operation of the vacuum pump 295.

When the vacuum pump 295 operates, a washing solvent remaining in wells in the specific well of the multi-well plate kit 210 is rapidly removed, and when the drying is completed, the vacuum module 291 moves to the position of the vacuum module rack 293 again to thereby be detached from the moving part body 610 and stored in the vacuum module rack 293.

In addition, after the moving part body 610 of the moving part 600 moves to a position of the pipette rack 510 for a next operation, the pipettes 500 fixed to a pipette block 630 is fixed again.

In other words, the drying part 290 does not use a separate composition for fixing and moving the vacuum module 291 but uses a composition of the moving part 600 operating the pipette 500, such that in the apparatus 1000 for automatically analyzing biological samples according to the present invention, a configuration of the entire apparatus may be simplified, and the apparatus 1000 may be easily operated.

Further, the apparatus 1000 for automatically analyzing biological samples according to the present invention has an advantage in that a time for drying the washing solvent in the purified target nucleic acid may be significantly decreased by including the drying part 290, such that the washing solvent having a negative influence on the amplification process may be rapidly removed.

The nucleic acid amplification part 400, which is a component amplifying the target nucleic acid purified by the purification part 200, is a component amplifying a target material purified by the purification part 200 (see FIGS. 20 and 21). The nucleic acid amplification part 400 may be formed to include amplification tubes 411, an amplification block cover 410, a heat transferring part 420, and an amplification tube fixing part 430.

The amplification tube 411 is a space in which reagents for amplifying the nucleic acid are embedded and is positioned so as to correspond to positions of wells 211 forming a single row in the multi-well plate kit 210 in a transverse direction, respectively. Further, although the case in which the amplification tube 411 is formed in two rows is shown by way of example in FIG. 20, the apparatus 1000 and method for automatically analyzing biological samples according to the present invention are not limited thereto, and one or more amplification tubes 411 may be variously formed as needed.

When the amplification tube 411 is formed in two rows, in the cases of PCR and isothermal amplification, tubes in first row are used. The amplified product embedded in amplification tube in a single row after amplification is moved to the electrophoresis part 300, and the amplified product embedded in the other row may be moved to the electrophoresis part 300 again to thereby be re-inspected, be used in a different test, or be separately stored.

In addition, in the case of amplifying genes using a RT-PCR method and a nested PCR method, the amplification tubes 411 embedded with different materials in two rows are used, and the amplification tubes in each of the rows may be regulated to a temperature suitable for each of the reaction steps.

More specifically, in the case of amplifying genes using the RT-PCR method, a reverse transcription reaction solution is in amplification tubes 411 in a first row, such that a reverse transcription reaction may be carried out by mixing the reverse transcription reaction solution with a target nucleic acid containing solution, and a PCR reaction solution is in amplification tubes 411 in a second row, such that a PCR reaction may be carried out by mixing the reactant of the reverse transcription reaction.

In the case of the nested PCR, a primary PCR reaction solution is in amplification tubes 411 in a first row, such that a primary PCR may be carried out by mixing the primary PCR reaction solution with a target nucleic acid containing solution, and a secondary PCR reaction solution is in amplification tubes 411 in a second row, such that a nested PCR reaction may be carried out by mixing the reactant of the primary PCR reaction.

A material required to perform each of the amplification processes is embedded in the amplification tubes 411, and a user may prepare an amplification process by a simple process of penetrating the amplification tube 411 through a second exposure hole 702 of the base plate 700, seating the amplification tubes 411 on seating grooves 421 of the amplification block cover 410, and fixing the amplification tube 411 using the amplification tube fixing part 430. The heat transferring part 420, which is a component heating and cooling the amplification tube 411, is formed under the amplification block cover 410 formed with the seating grooves 421 in which the amplification tube 411 is seated.

The heat transferring part 420 may have various shapes, and a peltier element 423 and a temperature sensor are used in order to easily control a temperature. The nucleic acid amplification part 400 includes the amplification block cover 410 to which a first fixed magnet 422 is insertedly adhered in order to fix the amplification tube 411 and the amplification tube fixing part 430 to which a second fixed magnet 431 corresponding to the first fixed magnet 422 is insertedly adhered. As the amplification tube fixing part 430 is formed so as to be supported by an upper portion of the amplification tube 411 to enclose the amplification tube 411, the amplification tube fixing part 430 stably and closely adheres the amplification tubes 411 to the seating grooves 421 to facilitate the transferring of the temperature and prevent the temperature from being changed, thereby increasing amplification efficiency. In this case, in order to closely adhere the amplification tube, it is preferable that a lower surface of the amplification tube fixing part 430 is formed to have a height so that a space S spaced apart from a surface in which the seating grooves 421 of the amplification block cover 410 are formed may be formed by a predetermined distance. In addition, a hollow second exposure hole 702 is formed in the base plate 700 so that the amplification tube 411 and the amplification tube fixing part 430 may be formed on an upper surface of the amplification block cover 410. In other words, the second exposure hole 702 is a component formed at a region at which the heat transferring part 420 is positioned when insertion of the base plate 700 into the case 100 is completed and has a size larger than that of the amplification tube fixing part 430. Since the base plate 700 is moved in the length direction of the case 100, the amplification tube 411 and the amplification tube fixing part 430 are fixed to the heat transferring part 420 through the second exposure hole 702 of the base plate 700 after the insertion of the base plate 700 into the case 100 is completed.

Further, the apparatus 1000 for automatically analyzing biological samples according to the present invention may further include a light irradiation part 440 irradiating excitation light toward the amplification tube 411; and a fluorescence detector 450 fixed to the moving part 600 to real-time measure an inside of the amplification tube 411 in the nucleic acid amplification part 400, as shown in FIGS. 18 and 19.

The light irradiation part 440 and the fluorescence detector 450 are components enabling real-time PCR, and a light emitting diode (LED) may be used as the light irradiation part 440.

The fluorescence detector 450 is configured so as to be movably fixed to the moving part 600, and may be formed so that a height may be individually adjusted as shown in FIGS. 3 and 4.

The fluorescence detector 450, which is a unit capable of measuring an amount of fluorescence through photographing, may be formed to include a photodiode, a lens, and a filter.

In the case in which the fluorescence detector 450 is formed, the first sterilization unit 800 may be positioned at a front portion of the fluorescence detector 450 in a region of the moving part 600.

The electrophoresis part 300, which is a component inspecting the amplified product through the nucleic acid amplification part 400, inspects a length and an amount of DNA.

More specifically, the electrophoresis part 300 is formed to include the electrophoresis body 310, a power supply part 320, an excitation light irradiation part 330, and a photographing part 350, and a power connection terminal 340 is formed at the base plate 700. First, the electrophoresis body 310, which is a component embedded with a material (for example, agarose gel) required for electrophoresis and performing an electrophoresis process, separates the amplified DNA by length. The power supply part 320 is a component provided at a bottom surface 140 of the case to supply direct current power to the electrophoresis body 310. The power connection terminal 340, which is a component fixed to the base plate 700, contacts with the power supply part 320 to connect power to the electrophoresis body 310. It is preferable that a protrusion part 341 protruding toward the electrophoresis body 310 is formed at the power connection terminal 340 so as to supply power simultaneously with fixation of the power connection terminal 340 and the electrophoresis body 310, and a hole type electricity connection terminal 311 into which the protrusion part 341 is inserted is formed in the electrophoresis body 310.

The excitation light irradiation part 330 is provided at the inner lower surface of the case 100 at a position on which the electrophoresis body 310 is seated to irradiate excitation light toward the electrophoresis body 310. In this case, the electrophoresis body 310 and a predetermined space of the base plate 700 in which the electrophoresis body 310 is seated are made of a material through which excitation light irradiated by the excitation light irradiation part 330 transmits. Meanwhile, since it is preferable that the excitation light irradiation part 330 uniformly irradiates light to the entire electrophoresis body 310, in the case in which the excitation light irradiation part 330 is formed of a plurality of LEDs, it is preferable that a light dispersion material layer made of a material scattering the excitation light, for example, a milk white acrylic material, is present in an electrophoresis body fixing plate 750 corresponding to a predetermined space of the base plate 700 on which the electrophoresis body 310 is seated. Further, LEDs mainly emitting light in an excitation light wavelength band are used in the excitation light irradiation part 330, and a bottom plate of the electrophoresis body 310 is made of a material entirely absorbing light in a fluorescence wavelength band of the nucleic acid included in the scattered excitation light while passing through the base plate 700 and maximally passing the light in the excitation light wavelength band, such that at the time of detecting fluorescence, background light is minimized, thereby maximizing sensitivity of the nucleic acid detection. As an example, in the case in which Sybr Green is used as a fluorescent dye of DNA, a blue colored material layer through which light passes is used.

The photographing part 350, which is a component photographing a state of electrophoresis, is configured of a lens capable of obtaining an image of an electrophoresis gel 362 on a charge coupled device (CCD) or complementary metal-oxide semiconductor (CMOS) sensor and a short-wavelength cut-off filter cutting off the excitation light incident on the lens and passing light in a wavelength band equal to or more than a fluorescence wavelength band generated from DNA. The photographing part 350 may photograph and transfer a progressing situation and a final result of electrophoresis (see FIG. 5). The photographing part 350 may be formed at an upper surface of the case 100, but more preferably, the photographing part 350 is formed at the moving part body 610 of the moving part 600, such that the photographing part 350 confirms a state of the electrophoresis part 300 at a more adjacent position. Here, in the case in which the photographing part 350 needs to be positioned adjacently to the electrophoresis body 310, the pipette 500 is stored in the pipette rack 510. The photographing part 350 is fixed to the moving part body 610 of the moving part 600, such that a photographing distance is decreased, such that there is an advantage in that the photographing may be performed with high sensitivity.

In addition, an elastic unit 321 is interposed at a lower portion of the power supply part 320 so that the power supply part 320 and the power connection terminal 340 are stably connected by insertion of the base plate 700, and it is preferable that as the base plate 700 is inserted into the case 100, first and second contact parts 342 and 322 contacting with and connected to each other are formed at lower surface of the power connection terminal 340 and upper surface of the power supply part 320. In addition, it is preferable that the first contact part 342 of the power connection terminal 340 is formed with a first inclined part 343 inclined in a central direction of the first contact part 342 at a corner portion thereof in an insertion direction of the base plate 700, and the second contact part 322 of the power supply part 320 is formed with a second inclined part 323 inclined in a central direction of the second contact part 322 at a corner portion thereof in a direction opposite to the insertion direction of the base plate 700 in the length direction of the case 100 so that the first contact part 342 of the power connection terminal 340 and the second contact part 322 of the power supply part 320 completely contact with each other. At the time of insertion of the base plate 700, while the first inclined part 343 of the power connection terminal 340 and the second inclined part 323 of the power supply part 320 contact with each other to thereby be guided, the elastic unit 321 is compressed, and the first contact part 342 of the power connection terminal 340 and the second contact part 322 of the power supply part 320 may strongly contact with each other at a final insertion position of the base plate 700, such that electricity may be easily transferred.

Further, in the apparatus 1000 for automatically analyzing biological samples according to the present invention, a gel tray 360 capable of allowing electrophoresis to be performed at the entire region of the electrophoresis body 310 may be used as shown in FIG. 22, and electrophoresis may be performed on only a half of the samples using a gel tray 360-1 allowing two electrophoresis gels 362 to put in the electrophoresis body 310 as shown in FIG. 23.

In the case shown in FIG. 23, a half of the biological samples and the pipette 500 may be mounted, and only a half of the samples are used in the purification part and the amplification part, and the remaining sample may be used later. In addition, in the electrophoresis part 310, a jaw may be formed at an upper portion of a circumference part thereof so that a solution required for electrophoresis does not overflow.

The case in which an electrophoresis gel fixing part 361 for fixing the electrophoresis gel 362 protrudes from lower surfaces of the gel trays 360 and 360-1 is shown by way of example in FIGS. 22 and 23.

The electrophoresis gel 362, which may be easily prepared by those skilled in the art, is prepared by boiling a solution containing agarose gel (1~5%), mounting a comb including loading wells 363 formed at the same position as a row of the pipettes 500 before the solution is solidified, positioning the gel tray 360 or 360-1 on a horizontal surface in a state in which both surfaces of the gel tray 360 or 360-1 are blocked, pouring the gel solution in a liquid state, and then cooling the poured gel solution. In this case, a hollow part of the gel corresponding to the electrophoresis gel fixing part 361 is formed to block the gel from moving in front and rear directions, such that at the time of loading the amplified product in the loading well 363 using the pipette 500, an accurate position may be maintained.

The apparatus 1000 for automatically analyzing biological samples according to the present invention may use an electrophoresis gel 362 having various shapes, and accordingly, a shape of the electrophoresis body 310 may also be changed in addition to the shape shown in the drawings.

In addition, in the apparatus 1000 for automatically analyzing biological samples according to the present invention, a marker storage part 900 embedded with a marker and a fluorescent dye material may be further formed in the electrophoresis part 300.

The marker storage part 900 has a configuration including a marker tube 920 embedded with the marker and the fluorescent dye material and a marker tube rack 910 mounted with the marker tube 920, and it is preferable that the marker tube rack 910 is detachably provided at the base plate 700 so that the marker may be easily embedded.

The pipette 500 is mounted in plural so as to form rows and is a component moving the biological samples, the samples or the reagent the purified target nucleic acid, and amplified DNA used in the entire regions of the purification part 200, the nucleic acid amplification part 400, and the electrophoresis part 300. In other words, the pipette 500, which is a component sucking and discharging the biological samples, the samples or the reagent the purified target nucleic acid, and amplified DNA, performs purification while moving to wells in first to N-th rows in the multi-well plate kit 210 of the purification part 200, transferring the purified target nucleic acid to the nucleic acid amplification part 400, and transferring the amplified DNA to the marker tube, the electrophoresis part 300, and the like.

The pipette 500 is a component transferring various materials in the entire apparatus 1000 for automatically analyzing biological samples of the present invention, and a plurality of pipettes 500 form rows. The number of pipettes 500 provided in a transverse direction while forming a single row is the same as the number of wells 211 positioned in a transverse direction of the multi-well plate kit 210.

In addition, it is preferable that the amplification tube 411 is also used so that the number of amplification tubes 411 is the same as the number of pipette 500 forming a single row and the number of wells 211 of the multi-well plate kit 210. Although the case in which twelve wells 211 of the multi-well plate kit 210 in transverse direction form eight rows, and the pipette 500 forms a single row is shown by way of example in the drawings, the apparatus 1000 for automatically analyzing biological samples according to the present invention is not limited thereto. In more detail, in order to increase the number of sample tested one time, a plurality of rows may be used, and twelve or more wells may be used.

The moving part 600 is a component capable of implementing the mounting, suction and discharge, detachment, and movement of the pipette 500 through the pipette block 630, and a detailed configuration of the moving part 600 for implementing the above-mentioned operations will be described below.

The moving part 600 may be configured using various shapes, and the shape shown in FIGS. 3 to 8 will be described below, but the apparatus 1000 for automatically analyzing biological samples according to the present invention is not limited thereto.

First, the moving part 600 moves in the length direction of the case 100. As an example, a support bar 150 is installed in the case 100 in the length direction, and a slider 621 is formed in the moving part body 610 and guided by the support bar 150 to thereby be moved in the length direction. In this case, an X axis moving motor 622 and an X axis moving belt 623 connected to the X axis moving motor 622 to move the moving part 600 may be formed in the moving part 600.

Next, a configuration for mounting the pipette 500 is shown in FIG. 6. Referring to FIG. 6, the apparatus 1000 for automatically analyzing biological samples according to the present invention includes a pipette mounting part including a pipette block fixing plate 644 to thereby mount the pipette 500 on the pipette block 630.

FIG. 6 is a view showing a state in which the pipette 500 is fixed to a pipette fixing protrusion part 644-1 by an operation of the pipette block fixing plate 644. Here, the pipette fixing protrusion part 644-1 is hided by the pipette 500, such that the pipette fixing protrusion part 644-1 is not shown (a configuration of the pipette fixing protrusion part 644-1 is shown in FIG. 8).

The pipette mounting part includes the pipette fixing protrusion part 644-1 on which the pipette is mounted, the pipette block fixing plate 644 formed with the pipette fixing protrusion part 644-1, and components allowing the pipette block fixing plate 644 to be movable in the height direction.

As the components allowing the pipette block fixing plate 644 to be movable in the height direction, the case in which a Z axis screw 641, a Z axis screw nut 645, a Z axis guide bar 646, a Z axis guide bar slide 647, a Z axis motor 642 fixed to the moving part body 610, and a Z axis moving belt 643 transferring rotation motion of the Z axis motor 642 to the Z axis screw 641 in order to rotate the Z axis screw 641 are formed is shown in FIG. 6.

In this case, when the Z axis motor 642 is operated, the pipette block fixing plate 644 is moved along the Z axis guide bar 646 by rotation of the Z axis screw 641 fixed to the moving part body 610.

That is, in the apparatus 1000 for automatically analyzing biological samples according to the present invention, as the Z axis motor 642 rotates, the pipette block fixing plate 644 is moved in the vertical direction, and the pipette fixing protrusion part 644-1 is inserted into an upper portion of the pipette 500 by the movement of the pipette block fixing plate 644 in a downward direction, such that the pipette 500 may be mounted.

Meanwhile, at the time of mounting the pipette 500, after a position of a piston 631 is sufficiently raised, the pipette 500 may be inserted by turning the Z axis screw 641 to allow the pipette block fixing plate 644 to descend toward the pipette 500.

In addition, it is preferable that the pipette 500 may be stably operated by installing devices relating to operations of the pipette 500 to the pipette block fixing plate 644 moving toward upper and lower portions of the moving part 600.

The pipette block 630 is mounted to the moving part body 610, which is a reference point of vertical movement of the pipette block fixing plate 644, to thereby adjust suction and discharge operations of the pipette 500. In addition, the pipette 500 may move in the length (X axis) and height (Z axis) directions of the case 100, and a configuration for adjusting suction and discharge of the pipette 500 will be described with reference to FIG. 7.

In the apparatus 1000 for automatically analyzing biological samples according to the present invention, suction and discharge of the pipette 500 may be adjusted through a pipette adjusting part including the piston 631 formed at the upper portion of the pipette block 630 and a piston fixing plate 634 fixed to the piston 631 and being movable in the height direction.

Here, the pipette block 630 includes the pipette adjusting part so as to be sealed with the pipette 500 as a component allowing the suction and discharge operations of the pipette 500 to be adjusted, wherein the pipette adjusting part includes the piston 631, the piston fixing plate 634, and a unit for moving the piston fixing plate 634 in the height direction (a unit capable of compressing the piston 631).

The unit for moving the piston fixing plate 634 in the height direction is formed to include a piston motor 632 vertically moving the piston 631, a piston moving screw 635 rotated by a piston belt 633, a piston moving screw nut 636 fixed to the piston fixing plate 634 to vertically move the piston fixing plate 634 by rotation of the piston moving screw 635, and the piston fixing plate 634 fixing the piston 631 and piston moving screw nut 636 on the piston 631.

The piston motor 632 may be provided on the uppermost plate supported by a piston guide bar 637 installed at the piston fixing plate 634.

For tuning vertical movement of the piston moving screw nut 636 and movement of the piston 631 to each other, the piston fixing plate 634 is installed on the pistons 631, and the pistons 631 and the piston moving screw nut 636 are fixed thereto.

Describing an operation, as the piston moving screw 635 is rotated, the piston fixing plate 634 moves in the vertical direction along the piston guide bar 637 guiding movement in vertical direction, such that the pistons 631 vertically moves in the pipette block 630 while maintaining the sealing to thereby perform the suction and discharge operations of the pipette 500.

An example for implementing detachment of the pipette 500 is shown in FIG. 8, and in the example shown in FIG. 8, a pipette extrusion plate 638-1, a pipette extrusion pin fixing plate 639, and pipette extrusion pins 638 are used.

More specifically, a region of the pipette extrusion plate 638-1 corresponding to the pipette fixing protrusion part 644-1 is hollow, and when the pipette 500 is mounted on the pipette fixing protrusion plate 644-1, the pipette extrusion plate 638-1 is positioned between a lower surface of the pipette block fixing plate 644 and an upper surface of the pipette 500 so as to contact each other.

The pipette extrusion pin fixing plate 639 is a plate shape positioned over the pipette block 630, and the pipette extrusion pin 638 has a length longer than a height of the pipette block 630 and connects the pipette extrusion plate 638-1 and the pipette extrusion pin fixing plate 639.

That is, the apparatus 1000 for automatically analyzing biological samples according to the present invention is characterized in that when the pipette extrusion pin fixing plate 639 is moved downwardly by an operation of the pipette adjusting part, the pipette extrusion pin fixing plate 639, the pipette extrusion pin 638, and the pipette extrusion plate 638-1 are moved downwardly to push the pipette 500, such that the pipette 500 is detached from the pipette fixing protrusion part 644-1.

In other words, in the apparatus 1000 for automatically analyzing biological samples according to the present invention, when the pipette 500 is mounted, the pipette extrusion plate 638-1 and the pipette extrusion pin 638 are pushed by the pipette 500, such that the pipette extrusion pin fixing plate 639 is pushed upwardly of the pipette block 630 to thereby be positioned to be spaced apart from an upper portion of the pipette block 630 by a predetermined interval as shown in FIG. 6. In order to detach the pipettes 500, in the case of turning the piston moving screw 635 to move the piston fixing plate 634 downwardly so as to contact with the upper portion of the pipette block 630, the piston fixing plate 634 pushes the pipette extrusion pin fixing plate 639, the pipette extrusion pin 638, and the pipette extrusion plate 638-1, the pipettes 500 may be detached as shown in FIG. 8.

The first sterilization unit 800 is a component fixed to the moving part 600, and an ultraviolet lamp may be used.

It is preferable that the first sterilization unit 800 is fixed, particularly to the fluorescence detector 450 among the entire components forming the moving part 600 in order to easily control a position thereof and allow the first sterilization unit 800 to be positioned so as to approach in the vicinity of a sterilization target. The case in which the first sterilization unit 800 is formed so as to be fixed to a side surface of the fluorescence detector 450 and irradiate ultraviolet rays or ozone downwardly is shown by way of example in FIG. 5. In addition, the apparatus 1000 for automatically analyzing biological samples according to the present invention may further include a reflection unit 810 so that a sterilization effect of the first sterilization unit 800 may be intensively exhibited at a specific position. The first sterilization unit 800 is used in order to inactivation of the genetically amplified product, and may be used in the vicinity of a gene amplification reaction vessel by an operation of the moving part 600 for inactivation of the genetically amplified product, such that inactivation of the genetically amplified product may be maximized.

In the apparatus 1000 for automatically analyzing biological samples according to the present invention, a second sterilization unit 820 formed of one of an ultraviolet lamp and an ozone generator may be further provided in the case in addition to the first sterilization unit 800. Further, the first sterilization unit 800 may sterilize each of the components of the purification part 200, the nucleic acid amplification part 400, the and electrophoresis part 300 through movement of the moving part 600, and the entire component may be sterilized by using the second sterilization unit 820.

Further, the apparatus 1000 for automatically analyzing biological samples according to the present invention may further include the base plate 700.

The base plate 700 has a composition in which the multi-well plate kit 210 and the electrophoresis body 310 are detachably provided, and the base plate 700 may be guided by a guide part 130 fixed to the lower surface of the case 100 to thereby be moved in the length direction of the case 100 through the opening part 110. In addition, as described above, the biological sample tube rack 280, the pipette rack 510, and the marker tube rack 910 may be provided in the base plate 700 so as to be mounted and detached. The multi-well plate kit 210 is embedded with the sample or reagent required for purification together with the biological samples, the electrophoresis body 310 is embedded with the material required for electrophoresis, and the marker tube 920 is embedded with the marker and the DNA fluorescent dye material required for electrophoresis. The base plate 700 is formed so that the multi-well plate kit 210, the electrophoresis body 310, the biological sample tube rack 280, the pipette rack 510, and the marker tube rack 910, which are components, may be mounted therein and detached therefrom. Therefore, there is an advantage in that a user may prepare analysis by a simple method of mounting and inserting each of the components. Meanwhile, the amplification tube 411 and the amplification tube fixing part 430, which are components directly fixed to the heat transferring part 420 through the second exposure hole 702 of the base plate 700, are fixed after the base plate 700 is inserted into the case 100.

The guide part 130 is formed at the inner lower surface of the case 100 for movement of the base plate 700 in the length direction, and a handle 710 is formed at an upper surface of one portion adjacent to the opening part 110, such that a user may easily take out the base plate 700 to mount the required components and insert the base plate 700.

Further, in the apparatus 1000 for automatically analyzing biological samples according to the present invention, for an accurate position at which the base plate 700 is inserted into and fixed the case 100, a first position fixing part 720 is formed at an end portion of the other portion (an opposite portion to the portion adjacent to the opening part 110) of the base plate 700, and a second position fixing part 120 fixed at a position of the case 100 corresponding to the first position fixing part 720 is formed, but the first and second position fixing parts 720 and 120 may be fixed to each other by magnetism. The shape in which a third fixed magnet 721 is formed at the first position fixing part 720 and fixed to the second position fixing part 120 is shown in FIG. 4. In addition, in the apparatus 1000 for automatically analyzing biological samples according to the present invention, the third fixed magnet 721 may be positioned at the second position fixing part 120, or the third fixed magnets 721 coupled to both of the first and second position fixing parts 720 and 120 may be respectively positioned. Further, the second position fixing part 120 may have a groove shape corresponding to a shape of the first position fixing part 720. Therefore, the apparatus 1000 for automatically analyzing biological samples according to the present invention has an advantage in that the position at which the base plate 700 is inserted into the case 100 may be determined, and the accurate position may be maintained as it is during an analysis process.

In addition, a waste liquid vessel 740 in which used waste liquids are stored may be detachably provided on the base plate 700.

The waste liquids are waste liquids discarded during a process of purifying the biological samples, and the like, and the waste liquid vessel 740 is detachably provided on the base plate 700 to thereby be easily used.

The control part is a component controlling the purification part 200, the nucleic acid amplification part 400, the electrophoresis part 300, and the moving part 600, and controls all of the components that need to be controlled in addition to the above-mentioned components.

Meanwhile, the method for automatically analyzing biological samples according to the present invention uses the apparatus 1000 for automatically analyzing biological samples as described above.

Therefore, in the method for automatically analyzing biological samples according to the present invention, the entire processes required for qualitatively analyzing sizes of amplified products through purification, amplification, and electrophoresis quantitative analysis are performed using a single apparatus (the apparatus 1000 for automatically analyzing biological samples according to the present invention), such that there are advantages in that inconvenience depending on using a plurality of apparatuses may be removed and entire analysis efficiency and accuracy may be increased.

The method for automatically analyzing biological samples using the apparatus 1000 for automatically analyzing biological samples according to the present invention will be described with reference to FIG. 24. The method includes a purification step (S10) of obtaining a target nucleic acid from the biological samples; an amplification step (S20) of amplifying the target nucleic acid purified in the purification step (S10); and an electrophoresis step (S30).

In addition, the purification step (S10) includes a pipette mounting step of moving the moving part 600 to insert the pipettes 500 into a fixed pipette block 630; and a target nucleic acid containing solution obtaining step of moving the moving part 600 to transferring/mixing biological samples contained in the biological sample tube and one or more samples or reagents required for purification, respectively embedded in wells in first to N-th rows in the multi-well plate kit 210 to obtain a target nucleic acid containing solution.

The target nucleic acid containing solution obtaining step includes a sample dissolving step of dissolving the biological sample including the target nucleic acid to elute the target nucleic acid; a target nucleic acid attaching step of attaching the target nucleic acid included in a homogeneous solution of the biological samples to magnetic particles and removing a solution of other biological materials; a magnetic particle washing step of removing other impurities of the magnetic particles including the target nucleic acid attached thereto; a magnetic particle drying step of removing the washing solvent contained in the magnetic particles; and an obtaining step of adding an elution solution for detaching the target nucleic acid attached to the magnetic particles.

In this case, in the purification step (S10), if necessary, a magnetic field applying step of applying a magnetic field to wells in a specific row in the multi-well plate kit 210 by the magnetic field application part 201 and a heat step of heating the wells in the specific row in the multi-well plate kit 210 by the heating part 202 are performed.

Further, in the magnetic particle drying step, after the pipettes 500 inserted into the moving part body 610 of the moving part 600 are detached and moved, the vacuum module 291 is inserted and then moved so as not to contact with an inner portion of the wells of the multi-well plate kit 210 including magnetic particles. Then, air is sucked and discharged by the vacuum pump 295. At the same time, the wells are heated by the heating part 202, such that a drying time of the washing solvent may be decreased.

In addition, the amplification step (S20) may include a mixing step of moving the target nucleic acid containing solution obtained through the purification step (S10) to the amplification tube 411 to perform the mixing; and a temperature regulating step of regulating a temperature by the heat transferring part 420 to perform amplification.

Describing the amplification step (S20) in more detail, the mixing step is a step of moving the moving part 600, fixing the pipettes 500 fixed to the moving part body 610 to move the target nucleic acid containing solution obtained through the purification step (S10) to the amplification tube 411 of the amplification part, and mixing the target nucleic acid containing solution with a reaction solution.

The temperature regulating step is a step of regulating the temperature by the heat transferring part 420 to perform amplification.

In this case, since in the nucleic acid amplification part 400 in which the amplification step (S20) is performed, the amplification tube 411 may be mounted in at most two rows, the amplification tubes 411 in a first row may be used, or the amplification tubes 411 in a second row may be used for another analysis later.

In addition, in the case of gene amplification using a RT-PCR method and a nested PCR method, the amplification tubes 411 embedded with different materials in two rows are used, and the amplification tubes in each of the rows may be regulated to a temperature suitable for each of the reaction steps.

More specifically, in the case of amplifying genes using the RT-PCR method, a reverse transcription reaction solution is in the amplification tubes 411 in the first row, such that a reverse transcription reaction may be carried out by mixing the reverse transcription reaction solution with the target nucleic acid containing solution, and a PCR reaction solution is in the amplification tubes 411 in the second row, such that a PCR reaction may be carried out by mixing the reactant of the reverse transcription reaction.

In the case of the nested PCR, a primary PCR reaction solution is in the amplification tubes 411 in the first row, such that a primary PCR reaction may be carried out by mixing the primary PCR reaction solution with a target nucleic acid containing solution, and a secondary PCR reaction solution is in the amplification tubes 411 in the second row, such that a nested PCR reaction may be carried out by mixing the reactant of the primary PCR reaction.

In this case, a sealing step for preventing evaporation of the reaction solution may be further performed between the mixing step and the temperature regulating step.

The sealing step is to prevent evaporation generated during the reaction due to an opened upper portion of the amplification tube 411 and may be performed by forming an evaporation prevention material on an upper layer portion of the reaction solution.

The evaporation prevention material needs not to be evaporated at 100° C., needs not affect the gene amplification reaction, and needs to be a light material having a specific gravity smaller than that of the reaction solution. As an example of the evaporation prevention material, mineral oil or paraffin melt at about 60 to 70° C. may be used.

If the paraffin capable of being used as the evaporation prevention material is contained in the amplification tube together with the reaction solution, the sealing step may be omitted.

The electrophoresis step (S30) includes a marker mixing step; an electrophoresis performing step; and an analyzing step.

The marker mixing step may be performed by moving the pipette 500 to the amplification tube 411 filled with the finally amplified product through the moving part 600, sucking the amplified product at a predetermined amount, and moving the pipette to the marker tube 910 filled with a solution containing the marker and the fluorescent dye material to mixing the amplified product and the marker solution with each other.

The electrophoresis performing step is a step of moving the amplified product mixed with the marker to an agarose gel loading well 363 of an electrophoresis body 310 to load the amplification product mixture on the agarose gel loading well and supplying power to the electrophoresis body 310 through the power supply part 320 and the power connection terminal 340 to perform electrophoresis.

The analyzing step is a step of irradiating light by an excitation light irradiation part 330 and confirming electrophoresis results using the photographing part 350.

At this time, as shown in FIG. 25, a preparation step (S40) may be further performed before the purification step (S10). The preparation step (S40) includes a first mounting step of taking out the base plate 700 to the outside of the case 100 and mounting the electrophoresis body 310, the pipette rack 510, the multi-well plate kit 210, the biological sample tube rack 280, the waste liquid vessel 740, the marker tube rack 910, and the marker tube 920 on the base plate 700; an inserting step of inserting the base plate 700 so that the first position fixing part 720 and the second position fixing part 120 contact with each other to thereby be fixed to each other; and a second mounting step of seating the amplification tubes 411 on the seating grooves 421 of the heat transferring part 420 exposed by the second exposure hole 702 of the base plate 700 and fixing the amplification tube 411 by an amplification tube fixing part 430.

In addition, an inactivation step may be further performed between the amplification step (S20) and the electrophoresis step (S30).

The inactivation step is to inactivate the amplified nucleic acid before the marker mixing step for performing the electrophoresis step (S30) after the gene amplification step (S20) and is a step of inactivating the amplified nucleic acid product by a photochemical reaction by moving the moving part 600 to move the fluorescence detector 450 including the first sterilization unit 800 attached thereto over the amplification tube 411 and operating the first sterilization unit 800 to irradiate ultraviolet rays.

As described above, the apparatus 1000 and method for automatically analyzing biological samples according to the present invention have advantages in that the entire processes of purifying, amplifying, and analyzing the target nucleic acid from the biological samples may be performed in the single apparatus, and analysis reliability and efficiency may be improved.

Meanwhile, according to the present invention, a method for obtaining a concentration of an antigen using quantitative immuno-PCR may be performed using the apparatus 1000 for automatically analyzing biological samples, such that the concentration of the antigen contained in the biological samples may be quantitatively measured by performing the quantitative immuno-PCR.

The present invention is not limited to the above-mentioned exemplary embodiments, and may be variously applied, and may be variously modified without departing from the gist of the present invention claimed in the claims.

The invention claimed is:

1. An apparatus for automatically analyzing biological samples, the apparatus comprising:
   a case including an opening structure formed so as to open a predetermined region;
   a base plate included in the case in such a manner as to be taken out from and inserted into the case through the opening structure;
   a purification structure including a multi-well plate kit in which a plurality of wells form first to N-th rows and wells in a specific row among the first to N-th rows are embedded with biological samples, and one or more samples or reagents required for purification to purify a target nucleic acid from the biological samples, said multi-well plate kit being detachably provided in the base plate;
   a nucleic acid amplification structure amplifying the target nucleic acid purified by the purification structure, the nucleic acid amplification structure comprising amplification tubes arranged in one or more rows, the amplification tubes being positioned so as to correspond to wells arranged in a single row in the multi-well plate kit in a transverse direction, respectively;
   an electrophoresis structure including an electrophoresis body to inspect an amplified product through the nucleic acid amplification structure and to analyze a size of the amplified product, said electrophoresis body being detachably provided in the base plate;
   a plurality of pipettes included in the case in rows to accommodate the biological samples and move the biological samples to the purification structure, the nucleic acid amplification structure, or the electrophoresis structure;
   a moving structure included in the case to move the pipettes in length and height directions of the case and adjust an operation of the pipettes, the moving structure comprising a moving structure body, said moving structure body being mounted in the base plate;
   a control structure controlling the purification structure, the nucleic acid amplification structure, the electrophoresis structure, and the moving structure; and
   a first sterilization unit comprising an ultraviolet lamp, the first sterilization unit being directly fixed to the moving structure,
   wherein the plurality of pipettes are mounted on the moving structure body, and
   wherein the moving structure is configured to move the first sterilization unit to a vicinity of the nucleic acid amplification structure.

2. The apparatus of claim 1, wherein the first sterilization unit further includes a reflection unit.

3. The apparatus of claim 1, wherein the purification structure further includes:
   a magnetic field application structure including a magnet to apply a magnetic field to wells in a specific row in the multi-well plate kit; and
   a heating structure formed adjacent to the magnetic field application structure to heat the wells in the same specific row.

4. The apparatus of claim 3, wherein the purification structure further includes a biological sample tube rack, the biological sample tube rack including biological sample tubes putting the biological samples for extracting the target nucleic acid,
   the biological sample tube rack being detachably provided in the base plate.

5. The apparatus of claim 3, wherein the magnetic field application structure includes:
   a magnet mounting structure on which the magnet is mounted; and
   a lift structure mounted on the lower surface of the case to lift up and down the magnet mounting structure.

6. The apparatus of claim 3, wherein the one or more samples or reagents required for purification, embedded in wells in the first to N-th rows in the multi-well plate kit include one or more of an enzyme, a cell lysate solution, a nucleic acid binding solution, an aqueous dispersion of magnetic particles, and a washing solution.

7. The apparatus of claim 5, wherein the magnet mounting structure comprises an insertion groove formed on a surface of the magnet mounting structure on which the magnet is mounted so that a lower portion of a specific row in the multi-well plate kit is inserted, and
   the base plate further comprises a first exposure hole at which a predetermined region is hollow so that the lower portion of the specific row is seated in the insertion groove at the time of lifting up the magnet mounting structure.

8. The apparatus of claim 7, wherein the magnet mounting structure is made of a metal material, and the heating structure is a heat generation film formed to contact with the magnet mounting structure.

9. The apparatus of claim 3, further comprising:
   a protrusion fixing structure protruding from a lower portion of the multi-well plate kit so as to be positioned between the plurality of wells; and
   an elastic unit provided on the protrusion fixing structure to thereby be closely adhered to the well,
   wherein the protrusion fixing structure and the elastic unit are provided in the base plate.

10. The apparatus of claim 6, further comprising a waste liquid vessel storing waste liquids discarded after being used, wherein the waste liquid vessel is detachably provided in the base plate.

11. The apparatus of claim 3, wherein
    the moving structure includes a pipette block capable of mounting and detaching the pipettes, and
    the apparatus further comprises a pipette rack capable of storing the pipettes that is detachably provided in the base plate.

12. The apparatus of claim 11, wherein the pipette block of the moving structure comprises:
    a pipette fixing protrusion structure of which the pipette mounted at a lower portion is formed, wherein the pipette is mounted on the pipette fixing protrusion structure through a pipette mounting structure including a pipette block fixing plate being movable in height direction.

13. The apparatus of claim 12, wherein the pipette block of the moving structure further comprises:
    a pipette adjusting structure including pistons formed at an upper portion thereof and a piston fixing plate including the pistons fixed thereto and being movable in the height direction,
    wherein suction and discharge of the pipette are adjusted by the pipette adjusting structure.

14. The apparatus of claim 13, wherein the pipette block of the moving structure includes:
    a pipette extrusion plate having a hollow region corresponding to the pipette fixing protrusion structure and positioned so as to contact between a lower surface of the pipette block fixing plate and an upper surface of the pipette when the pipette is mounted, a pipette extrusion pin fixing plate positioned over the pipette block, and pipette extrusion pins having a length longer than a height of the pipette block and connecting the pipette extrusion plate and the pipette extrusion pin fixing plate to each other, when the pipette extrusion pin fixing plate is moved downwardly by an operation of the pipette adjusting structure, the pipette extrusion pin fixing plate, the pipette extrusion pins, and the pipette extrusion plate being moved downwardly, and the pipette being detached from the pipette fixing protrusion structure.

15. The apparatus of claim 11, wherein the purification structure further includes a drying structure including a vacuum module capable of being detached from/attached to the moving structure, a vacuum module rack mounted on an inner lower surface of the case to store the vacuum module at a predetermined position, and a vacuum pump connected to the vacuum module through a hose.

16. The apparatus of claim 15, wherein in the drying structure, a convex structure is formed to protrude from an upper surface of the vacuum module rack, and a concave structure corresponding to the convex structure is formed at a lower surface of the vacuum module.

17. The apparatus of claim 16, wherein in the drying structure, a support structure supporting one portion of the vacuum module is provided at the vacuum module rack, and a magnet is embedded at surfaces of the support structure and the vacuum module contacting with each other.

18. The apparatus of claim 1, wherein the electrophoresis body includes electricity connection terminals having a hole, the electricity connection terminals are connected to electrode lines that form positive and negative electrodes, respectively; and wherein the electrophoresis structure further includes:
an electricity connection terminal having a protrusion and inserted into the electricity connection terminal of the electrophoresis body for connecting power;
a power supply structure fixed to an inner surface of a lower portion of the case to supply power to the electrophoresis body;
an excitation light irradiation structure irradiating excitation light to the electrophoresis body; and
a photographing structure photographing a state of electrophoresis.

19. The apparatus of claim 18, wherein the electrophoresis structure further comprises:
a first contact structure and a second contact structure contacting with and connected to each other when the base plate is inserted into the case, wherein the first contact structure and the second contact structure are formed to be inclined at a lower surface of a power connection terminal and an upper surface of the power supply structure, and closely adhered to each other by an elastic unit at a lower portion of the second contact structure of the power supply structure.

20. The apparatus of claim 18, wherein the excitation light irradiation structure comprises:
light emitting diodes (LEDs) irradiating light in an excitation light wavelength band toward the electrophoresis body, wherein the LEDs are provided on an inner lower surface of the case at equidistance,
the electrophoresis body fixing plate of the base plate on which the electrophoresis body is seated, wherein the electrophoresis body fixing plate comprises a material scattering the excitation light, and a bottom plate of the electrophoresis body comprising a material absorbing light in a fluorescence wavelength band of the nucleic acid and passing the light in an excitation light wavelength band.

21. The apparatus of claim 18, wherein the photographing structure comprises an image sensor, a lens, and a short wavelength filter and is fixed to the moving structure body of the moving structure.

22. The apparatus of claim 18, wherein the electrophoresis structure further includes a marker storage structure including marker tubes embedded with a marker and a fluorescent dye material and a marker tube rack mounted with the marker tubes, the marker tube rack being detachably provided in the base plate.

23. The apparatus of claim 18, wherein the electrophoresis body further includes a gel tray, the gel tray including an electrophoresis loading well formed at a bottom thereof and a plurality of electrophoresis gel fixing structure formed at position that is not overlapped with an electrophoresis moving path.

24. The apparatus of claim 1, wherein the nucleic acid amplification structure includes:
amplification tubes arranged in one or more rows;
an amplification block comprising concave seating grooves closely adhered to a lower portion thereof and made of a metal into which a temperature sensor is inserted;
an amplification block cover made of a heat insulation material provided with a first fixed magnet;
a peltier element;
a heat transferring structure transferring heat generated in the peltier element to the outside; and
an amplification tube fixing structure formed with holes smaller than an upper surface of the amplification tube, formed so as to enclose a predetermined region of an upper portion of the amplification tube, including a second fixed magnet inserted thereinto so as to correspond to the first fixed magnet and fix the amplification tube, and having a height spaced apart from a surface on which the amplification block cover is formed by a predetermined distance.

25. The apparatus of claim 24, wherein the base plate further comprises a hollow second exposure hole so that the amplification block and the amplification block cover correspond to the amplification tube fixing structure.

26. The apparatus of claim 24, wherein the nucleic acid amplification structure is positioned adjacent to the opening structure.

27. The apparatus of claim 24, wherein the nucleic acid amplification structure further includes:
a light irradiation structure irradiating fluorescent excitation light toward the amplification tube; and
a fluorescence detector provided movably in a vertical direction so as to be closely adhered to the upper portion of the amplification tube to real-time measure an amount of fluorescence in the amplification tube.

28. The apparatus of claim 1, wherein the base plate further comprises a handle at an upper surface of one portion adjacent to the opening structure.

29. The apparatus of claim 1, wherein the case further includes an air flow structure forming a channel through which air flows at an outer lower surface thereof and an air blower blowing air to the air flow structure.

30. The apparatus of claim 1, further comprising:
a first position fixing structure is further formed at an end portion of a portion of the base plate; and a second position fixing structure fixed to the case and formed at a position corresponding to the first position fixing structure, wherein the first and second position fixing structures are fixed to each other by magnetism of a third fixed magnet.

* * * * *